(12) United States Patent
Newman et al.

(10) Patent No.: US 6,869,606 B1
(45) Date of Patent: Mar. 22, 2005

(54) BIOTINYLATED-CHEMOKINE ANTIBODY COMPLEXES

(75) Inventors: Walter Newman, Boston, MA (US); Dominic Picarella, Sudbury, MA (US); Dulce Soler, Watertown, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/507,146

(22) Filed: Feb. 18, 2000

Related U.S. Application Data

(60) Provisional application No. 60/121,006, filed on Feb. 22, 1999.

(51) Int. Cl.[7] .................. A61K 39/395; A61K 38/00; C07K 16/18; C07D 49/34
(52) U.S. Cl. .................. 424/178.1; 514/2; 530/391.7; 530/807; 530/389.8; 530/387.3; 530/388.25; 548/303.7; 549/69
(58) Field of Search .................. 424/178.1, 138.1, 424/139.1, 136.1, 159.1, 181.1, 183.1; 514/2, 21; 530/350, 387.3, 388.25, 389.8, 391.7, 807, 307, 308, 311, 314, 315, 316, 387.1, 387.7, 388.1, 388.2, 388.23, 388.3, 388.8, 388.9, 309; 548/303.7; 549/69

(56) References Cited

U.S. PATENT DOCUMENTS

| | | | |
|---|---|---|---|
| 5,428,130 A | 6/1995 | Capon et al. | 530/350 |
| 5,518,882 A | 5/1996 | Lund et al. | 435/6 |
| 5,607,659 A | 3/1997 | Gustavson et al. | 424/1.73 |
| 5,645,835 A | 7/1997 | Fell, Jr. et al. | 424/134.1 |
| 5,700,444 A | 12/1997 | Zamora et al. | 424/1.69 |
| 5,716,594 A | 2/1998 | Elmaleh et al. | 424/1.41 |
| 5,759,515 A | 6/1998 | Rhodes et al. | 424/1.69 |
| 5,780,426 A | 7/1998 | Palladino et al. | 514/9 |
| 5,807,879 A | 9/1998 | Rosebrough | 514/387 |
| 5,824,782 A | 10/1998 | Holzer et al. | 530/391.1 |
| 5,830,851 A | 11/1998 | Wrighton et al. | 514/2 |
| 5,834,419 A | 11/1998 | McFadden et al. | 514/2 |
| 5,929,066 A * | 7/1999 | McCarty | |
| 6,214,450 B1 * | 4/2001 | Wickert et al. | |
| 6,303,325 B1 * | 10/2001 | Mehta et al. | |
| 6,638,508 B2 * | 10/2003 | Schechter et al. | 424/157.1 |

FOREIGN PATENT DOCUMENTS

| | | |
|---|---|---|
| EP | 0 217 577 | 4/1987 |
| EP | 337746 * | 10/1989 |
| EP | 0 460 569 A1 | 12/1991 |
| WO | WO 96/40251 | 12/1996 |
| WO | WO 98/33914 | 8/1998 |
| WO | WO 98/38212 | 9/1998 |
| WO | WO 00/12554 | 3/2000 |
| WO | WO 00/42071 | 7/2000 |

OTHER PUBLICATIONS

Abstract of Tromholt et al (Journal of Nuclear Medcine, 1991, vol. 32, pp. 2318–2321).*

Batra, Raj K., "Receptor–Mediated Gene Delivery Employing Lectin–Binding Specificity," *Gene Therapy*, 1:4, pp. 255–260 (1994) (Abstract).

Hechtman, D.H. et al., "Inhibitor of Polymorphonuclear Leukoctye Accumulation at Sites of Acute Inflammation," *The Journal of immunology*, vol. 147, (1991), pp. 883–892.

Mock, D.M. et al., "Distribution of Biotin in Human Plasma: Most of the Biotin Is Not Bound to Protein," *Am. J. Clin. Nutr.*, (1992) vol. 56, No. 2., pp. 427–432—Abstract Only.

Dale, G.L. et al., "Antibodies Against Biotinylated Proteins Are Present in Normal Human Serum," *J. Lab. Clin. Med.* (1994), vol. 123, No. 3, pp. 365–371—Abstract Only.

Bagei, H. et al., Monoclonal Anti–Biotin Antibodies Simulate Avidin in the Recognition of Biotin, *FEBS 12391*, vol. 322, No. 1 (1993), pp. 47–50.

Challita–Eid, P.M. et al., "A Rantes–Antibody Rusion Protein Retains Antigen Specificity and Chemokine Function," *The Journal of Immunology*, 1998, vol. 161, pp. 3729–3736.

Lussow, A.R. et al., "Targeting of Antihapten Antibodies to Activated T Cells Via an II–2–Hapten Conjugate Prolongs Cardiac Graft Survival," *Transplantation*, (1996), vol. 62, pp. 1703–1708.

Gimbrone, Jr., M.A. et al., "Endothelial Interleukin–8: A Novel Inhibitor of Leukocyte–Endothelial Interactions," *Science*, vol. 246, (1989), pp. 1601–1603.

* cited by examiner

*Primary Examiner*—Karen A. Canella
(74) *Attorney, Agent, or Firm*—Wolf, Greenfield & Sacks, P.C.

(57) ABSTRACT

Biotinylated pharmacologically active agents and complexes containing same are disclosed. In particular, biotinylated-chemokines are described. The complexes further include an anti-biotin antibody that selectively binds to biotin. The complex can be dissociated by contact with free biotin. The complexes are particularly useful for enhancing an immune response to tumor cells and virus-infected cells, in vivo or in vitro.

68 Claims, 8 Drawing Sheets

BIOTINYLATED-CHEMOKINE ANTIBODY COMPLEXES

This application claims priority under Title 35 § 119 (e) of United States Provisional Application No. 60/121,006, filed Feb. 22, 1999, and entitled BIOTINYLATED CHEMOKINE ANTIBODY COMPLEXES, the entire contents of which are incorporated herein by reference.

FIELD OF THE INVENTION

This invention relates to biotinylated compounds that, optionally, are complexed with an anti-biotin antibody or fragment thereof. More specifically, the invention relates to complexes comprising biotinylated-chemokines and an antibody or fragment thereof selectively bound to the biotin. The biotinylated-chemokines and complexes containing same are useful for modulating the mechanism underlying a variety of disease states, including a chemokine-mediated cellular response, and for the selective delivery of agents to sites of disease activity.

BACKGROUND OF THE INVENTION

Chemokines are a class of cytokine molecules that are involved in cell recruitment and activation in inflammation. These chemokines have been classified into four subgroups, depending on the nature of the spacing of two highly-conserved cysteine amino acids that are located near the amino terminus of the polypeptide. The first chemokine subgroup is referred to as "CXC"; the second subgroup is referred to as "CC"; the third chemokine subgroup is referred to as "CX3C"; and the fourth chemokine subgroup is referred to as "C". Within these subgroups, the chemokines are further divided into related families that are based upon amino acid sequence homology. The CXC chemokine families include the IP-10 and Mig family; the GROα, GROβ, and GROβ family; the interleukin-8 (IL-8) family; and the PF4 family. The CC chemokine families include the monocyte chemoattractant protein (MCP) family; the family including macrophage inhibitory protein-1α (MIP-1α), macrophage inhibitory protein-1 β (MIP-1 β), and regulated on activation normal T cell expressed (RANTES). The stromal cell-derived factor 1α (SDF-1α) and stromal cell-derived factor 1β (SDF-1β) represent a chemokine family that is approximately equally related by amino acid sequence homology to the CXC and CC chemokine subgroups. The CX3C chemokine family includes fractalkine; The C chemokine family includes lymphotactin. In general, the CXC chemokines are bound by members of the CXCR class of receptors; the CC chemokines are bound by the CCR class of receptors; the CX3C chemokines are bound by the CX3CR class of receptors; and the C chemokines are bound by the CR class of receptors.

Cells which express chemokine receptors include migratory cells such as lymphocytes, granulocytes, and antigen-presenting cells (APCs) that are believed to participate in immune responses or that may release other factors to mediate other cellular processes in vivo. The presence of a chemokine gradient serves to attract migratory cells which express the chemokine receptors. For example, migratory cells can be attracted by a chemokine gradient to a particular site of inflammation, at which location they play a role in further modifying the immune response. Chemokine receptors also are involved in interacting with viral proteins. In particular, CXCR4(fusin), CCR5, and other chemokine receptors have been identified as co-receptors for HIV-1 and HIV-2. In addition, chemokine receptors are expressed on a variety of non-motile cells such as neurons, microglia, epithelial cells and fibroblasts. Chemokines are also known to affect a variety of non-migratory cell functions such as granule release, cytokine release, angiogenesis, growth and differentiation. However, the half-life for chemokines in vivo is relatively short. (See, e.g., D. Hechtman, et al., J. Immunol. 147(3): 883–892 (1991) which reports a decline to preinjection levels of IL-8 in 30 minutes).

Various approaches also have been tried to extend the half-life of injected chemokines in vivo, as well as to accomplish the targeted delivery of chemokines to cell populations to establish a chemokine gradient. For example, International Application No. PCT/US98/04002, (Publication No. WO 98/38212, inventors S. Herrmann and S. Swanberg), entitled "Chimeric Polypeptides Containing Chemokine Domains," reports a chimeric DNA molecule comprising a sequence encoding a chemokine polypeptide covalently attached to a heterologous polypeptide such as the binding domain of an antibody. Similarly, International Application No. PCT/US98/01785, (Publication No. WO 98/33914, inventors J. Rosenblatt, et al.,), entitled "Chimeric Antibody Fusion Proteins for the Recruitment and Stimulation of an Antitumor Immune Response," reports chimeric molecules which include a binding region which specifically binds to a tumor-specific antigen and a chemokine and/or co-stimulatory ligand. U.S. Pat. No. 5,645,835, issued to H. Fell, Jr. and M. Gayle, entitled "Therapeutic Antibody based Fusion Proteins," also reports an antibody-based fusion protein which includes an immunoglobulin portion coupled to a biologically active lymphokine. Unfortunately, each of the foregoing methods requires the creation of a chemokine fusion protein, thereby necessitating the development of tailored methods for the generation of each different chemokine construct. Thus, despite the innovations advocated in connection with fusion protein technology, there exists no universal approach for the targeted delivery of chemokines to cells which express the cognate chemokine receptor. Accordingly, a need still exists for a generally applicable method of chemokine delivery to cells in vivo or in vitro. Preferably, the universal method would be one which is easily reversible in vivo or in vitro.

SUMMARY OF THE INVENTION

The present invention overcomes these and other obstacles by providing a biotinylated-chemokine antibody complex that can be reversibly dissociated in the presence of free biotin. Accordingly, the invention provides a method by which the concentration of biotinylated-chemokine antibody complex can be adjusted by exposing the complex to varying amounts of free biotin in vivo or in vitro. The complexes of the invention are useful for a variety of applications, including modulating an immune response such as one which is mediated by the chemokine-induced recruitment of migratory cells to a site of inflammation, as well as for the targeted delivery of agents to cells which express a chemokine receptor. In a broader aspect, the invention embraces biotinylated peptide ligands that bind to G-protein coupled receptors. Thus, the invention permits the targeted delivery of agents (diagnostic and therapeutic agents) to pre-selected cells which express such receptors and, advantageously, both avoids the necessity for the synthesis of individual fusion proteins to accomplish these objectives and provides a mechanism for rapid down regulation of activity.

According to one aspect of the invention, a composition is provided which includes at least one type of each of the following components: (a) a biotin conjugate (also referred to as a "biotinylated agent"), including: (i) a biotin covalently coupled to (ii) a pharmacologically active agent; and (b) an anti-biotin antibody. The anti-biotin antibody is selectively bound to the biotin to form a complex of the invention. The composition optionally further includes a pharmaceutically acceptable carrier and may be formulated for a variety of modes of delivery in vivo, including intradermal, intramuscular, intraperitoneal, intravenous, subcutaneous, and controlled-release delivery. The preferred pharmacologically active agents are chemokines, although other peptide ligands which bind to G-protein coupled receptors also are embraced within the broader aspects of the invention.

Biotin is a naturally occurring enzyme cofactor in its L isomeric form. Although it is preferred that L biotin be used for forming the biotin conjugates of the invention, the invention also embraces the D isomeric form of biotin, as well as other biotin derivatives. In general, the biotin is conjugated to the pharmacologically active agent (e.g., chemokine) by way of a linker molecule to form a "biotin conjugate". Thus, as used herein, the phrase "a biotin" embraces the D and L isomeric forms of biotin and biotin derivatives in which biotin is coupled to a linker molecule. The linker molecule is selected to have a structure and to provide a sufficient distance between the biotin and the pharmacologically active agent to ensure that the presence of the biotin and/or the linker molecule does not adversely affect the pharmacological activity of the agent. Such linker molecules are well known in the art for coupling peptides and proteins to one another and for the attachment of other functional molecules to proteins.

According to certain preferred embodiments, the biotinylated pharmacologically active agents are peptides which selectively bind to G-protein coupled receptors. Exemplary peptide ligands which bind to G-protein coupled receptors include Angiotensin; Bradykinin; Bombesin/Neuromedin; C3a; C5a; Calcitonin; Calcitonin Gene Related Peptide; Chemokine; Cholecystokinin; Conopressin; Corticotropin Releasing Factor (CRF); CD55— Decay Accelerating Factor (DAF); Diuretic Hormone Receptors; Endothelin; MLP; FSH Glycoprotein Hormone; Galanin; Growth Hormone Releasing Hormone (GHRH); Growth Hormone Secretagogue (GHS); Gastric Inhibitory Peptide; Gastric Inhibitory Peptide; Glucagon-like Peptide; Glucagon; Gonadotropin Releasing Hormone; LH Glycoprotein Hormone; Melanocortin Receptors; Neuropeptide Y; Neurotensin; Opioid; Oxytocin; Thrombin and Protease Activated; Pituitary Adenylyl Cyclase Activating Peptide; PTH/PTHrP; Secretin; Somatostatin; Tachykinin; Thyrotropin Releasing Hormone; TSH Glycoprotein Hormone; Vasopressin; Vasotocin; Vasoactive Intestinal Peptide (VIP). In the preferred embodiments, the pharmacologically active agents are chemokines. Exemplary chemokines are provided in Table 1 for use in accordance with the methods of the invention. The Tables are located immediately preceding the claims. In general, biotin is coupled to the pharmacologically active peptide via a linker molecule. More specifically, for peptides which are chemokines, biotin is coupled via a linker to the carboxyl terminus of the chemokine. The biotinylated-chemokines of the invention embrace biotin coupled to the complete sequence of the chemokine, as well as biotin coupled to truncated or elongated versions of such peptides (e.g., a chemokine peptide which lacks a portion of its amino terminal or carboxyl terminal sequences). Although not wishing to be bound by any particular mechanism or theory, it is believed that interaction of the chemokine highly basic carboxyl terminus with the negatively charged glucosaminoglycans mediates the cellular uptake of chemokines and that truncation or deletion of the highly basic carboxyl terminus of chemokines can be used to create novel chemokine agonists having improved half-life characteristics. The invention also embraces biotinylated truncated or elongated chemokine peptides, in particular, at the amino terminus, for use as chemokine antagonists to inhibit the normal pharmacological activity of the chemokine. (See, e.g., D. Hechtman, et al., J. Immunol. 147(3): 883–892 (1991) which reports an IL-8-like inhibitor of polymorphonuclear leukocyte accumulation at sites of acute inflammation).

The complexes of the invention further include an antibiotin antibody which selectively binds to biotin in the biotin conjugate. As used herein, the term "antibody" embraces intact antibodies as well as antibody fragments, e.g., Fab'$_2$ fragments, CDR3 regions. Preferably, the anti-biotin antibody is a human, humanized, or primatized antibody and is non-antigenic in humans. The anti-biotin antibodies of the invention have a biotin binding domain that selectively binds to biotin alone or coupled to a linker molecule. One distinguishing feature of the anti-biotin antibodies of the invention, when complexed to a biotin conjugate, is a half-life of the complex which is significantly greater than the half-life of the free chemokine (not conjugated or associated in a complex) or biotinylated chemokine. Thus, in contrast to free chemokine which exhibits a short half-life in vivo (see, D. Hechtman, et al., supra.) the complexes of the invention have a half-life on the order of one day to one month (more preferably, from about one week to about two weeks). Moreover, the effective half-life of the complex can be attenuated by contacting the complex with biotin (in vivo or in vitro) to shift the equilibrium in the direction of complex dissociation. Thus, the anti-biotin antibodies of the invention are selected which permit the dissociation of the antibody from the biotin conjugate only in the presence of supra physiological levels of free biotin (alone or coupled to the linker molecule), i.e., the complex will not become dissociated under the conditions of physiologic biotin concentrations. Physiological concentrations of biotin in blood are approximately 0.5 nMol/liter or 122 ng/L (122 pg/ml). As used herein, superphysiological concentrations are defined as at least ten-fold, more preferably at least 100-fold and, most preferably, at least 1000-fold greater than the physiological concentration of the particularly agent being considered. Thus, in contrast to the fusion proteins of the prior art, the invention provides a mechanism by which the antibody can be selectively dissociated from the biotinylated chemokine, e.g., by contacting the complex with superphysiological concentrations of an exogenous source of free biotin under conditions which shift the equilibrium reaction in favor of complex dissociation. Accordingly, the antibodies of the invention are selected, in part, based upon their ability to dissociate from the biotinylated pharmacologically active agent in the presence of exogenous biotin.

Preferably, the antibodies of the invention, when complexed, exhibit a half-life of the complex that is significantly shorter than the half-life of an avidin-biotin complex in the presence of a supra physiological level of free biotin. The half-life of the complex in the presence of a supra physiological level of free biotin can be determined in accordance with routine procedures known to those of ordinary skill in the art. Thus, in contrast to the avidin-biotin complex, the half-life for the complexes of the invention are at least one-tenth, preferably one-one hundredth, and, more preferably, one-one thousandth of the half-life of the avidin-biotin complex in the presence of a supra physiological level of free biotin. More particularly, the half-life for a preferred complex of the invention in the presence of a supra physiological level of free biotin, with respect to the dissociation of biotin from the anti-biotin antibody, is less than about one hour, more preferably less than about 0.5 hours and, most preferably, less than about 15 minutes. Exemplary anti-biotin antibodies that are publicly available and that can be tested in screening assays to determine whether the antibody exhibits an acceptable dissociation rate constant and/or affinity constant for use (or further modification for use) in accordance with present invention are identified below.

Optionally, the antibodies of the invention further include a diagnostic or therapeutic agent for targeted delivery to a cell which expresses a receptor for the pharmacological agent (e.g., chemokine receptor). Exemplary therapeutic and diagnostic agents are described below.

In certain preferred aspects of the invention, the anti-biotin antibody exhibits a multi-specificity, preferably, a dual specificity. By this it is meant that the antibody includes a first binding domain which selectively binds to biotin and a second binding domain which selectively binds to at least one other molecule. For example, the antibody can exhibit a second specificity for a second biotin molecule, a tumor cell associated antigen, or a viral associated antigen. Exemplary tumor associated antigens are those from the following types of tumor cells: breast cancer cells, ovarian cancer cells, lung cancer cells, prostate cancer cells, as well as other, for example, her2-neu expressing cancer cells. In general, the tumor cell associated antigens are cell-surface antigens. More specific examples of tumor associated antigens include carcinoembryonic antigen (tumors of epithelial origin, such as colon, lung, and breast and their metastases), EGF-R (bladder and breast cancer), prostate specific membrane antigen (prostate cancer), GD)2 (neuroblastoma), membrane immunoglobulins (lymphomas), and T-cell receptors (T-cell lymphoma). Exemplary viral associated antigens include: gp120 of HIV, HbsAg, immediate and early genes of hepatitis C virus, CMV, Epstein Barr virus, and respiratory syncytial virus.

In certain preferred embodiments, the complex includes a biotin conjugate containing a chemokine that is involved in the recruitment of migratory cells which mediate a TH1 response, and the antibodies of the invention selectively bind to a tumor cell associated antigen and to the biotinylated-chemokine. According to this embodiment, the complex of the invention is delivered to tumor cells which express the tumor cell antigen and, thereby, mediates recruitment of TH1-type cells to the location of the tumor cells to enhance a localized TH1 immune response. In yet other embodiments, the antibodies of the invention exhibit a dual specificity to permit recruitment of pre-selected TH2-type cells to a location to treat a localized site of inflammation.

According to yet another aspect of the invention, a biotin composition comprising a therapeutically effective amount of a biotin of the invention and a pharmaceutically acceptable carrier is provided. The biotin composition is useful for administration to a patient who has or will receive a biotinylated-pharmacologically active agent antibody complex of the invention. Administration of the biotin composition facilitates dissociation of the complex in vivo and, thereby, allows one of ordinary skill in the art to further adjust the half-life of the complex in vivo. In general, the half-life of a biotinylated-chemokine of the invention is longer when the biotin conjugate is complexed with an anti-biotin antibody of the invention and is shorter when the biotin conjugate is present "free" (uncomplexed) in vivo. Accordingly, dissociation of the complex in vivo results in hastening the natural degradation of the biotin conjugate in vivo. The biotin composition also can be used to adjust the concentration in vitro.

The biotin composition can be administered in a variety of methods and, preferably, is administered in an oral form. In general, the therapeutically effective amount of biotin is significantly greater for the oral biotin composition of the invention compared to dietary biotin supplements. Typically, the oral biotin compositions of the invention are at least 10-fold, preferably 100-fold, and, more preferably, at least 1,000-fold greater than the concentration of biotin in dietary supplements. In the preferred embodiments, the therapeutically effective amount of biotin that is present in the biotin composition is from about 100 μg to about 100 mg. More preferably, the effective amount of biotin is from about 100 μg to about 10 mg and, most preferably, the effective amount of biotin is from about 1 mg to about 10 mg.

According to yet another aspect of the invention, a composition comprising a mixture of biotin conjugates is provided. The composition includes: (a) a first biotin conjugate, including (i) a first biotin covalently coupled to (ii) a first agent having a first pharmacological activity; and (b) a second biotin conjugate, including (i) a second biotin covalently coupled to (ii) a second agent having a second pharmacological activity. The first biotin and the second biotin may be the same or different. For example, the first biotin may include a linker which differs from that included in the second biotin. Regardless of the nature of the biotin, the biotins are coupled to the first and second agents, respectively, in a manner which does not adversely affect (diminish to a significant extent) the first and second pharmacological activities. Preferably, the first agent and the second agent represent different chemokines which bind to different receptors expressed on the same or different cell types. The composition, optionally, further includes an anti-biotin antibody that binds to the first biotin conjugate and/or the second biotin conjugate. Thus, the composition also provides a means of reversibly attaching two or more chemokines by way of an anti-biotin biotin antibody. Accordingly, the complexes of the invention can be used to target different categories of pre-selected chemokine receptors, e.g., CCR2 and CXCR3 receptors, without requiring de novo fusion protein construction. In yet other embodiments, the anti-biotin antibody has a dual specificity for binding to biotin and to an antigen expressed on the surface of a pre-selected cell. For example, a first anti-biotin antibody can be used to target a receptor that is expressed on a cytotoxic T-cell (e.g., CD8), and a second anti-biotin antibody can be used to target a receptor that is expressed on a monocyte or a virus-infected cell. In this manner, the complexes of the invention containing the same or different chemokines can be delivered to the same or different cell types.

According to yet another aspect of the invention, a biotin conjugate composition is provided. The composition includes the above-described biotin conjugate of the invention and a pharmaceutically acceptable carrier. The biotin conjugate includes a biotin covalently coupled to an agent having a pharmacological activity (e.g., a chemokine). Preferably, the pharmaceutically acceptable carrier is one which is tailored for in vivo use, particularly parenteral use. Exemplary pharmaceutically acceptable carriers are disclosed below.

According to still another aspect of the invention, a method for treating inflammation in a subject is provided. As used herein, the word treating embraces preventing, inhibiting, and ameliorating the symptoms of the particular condition which is being treated. The method of treatment involves: administering to a subject in need of such treatment a therapeutically effective amount of a biotin conjugate or of a complex comprising: (a) a biotin conjugate and an anti-biotin antibody. The biotin conjugate includes: (i) a biotin covalently coupled to (ii) an agent that selectively binds to a receptor expressed by a pre-selected cell associated with inflammation (e.g., a migratory cell). Administration of the biotin conjugate or the complex prevents or reduces inflammation in the subject. In certain embodiments, the biotin conjugate(s) and the anti-biotin antibody are simultaneously or sequentially administered to the subject. In the most preferred embodiments, the biotin conjugate is a biotinylated chemokine. Exemplary chemokines that can be used as the agent to which biotin is coupled in this aspect of the invention are provided in Table 1. In certain preferred embodiments, the pre-selected cell is a migratory cell, such as a T-cell or leukocyte, and the administration of a complex enhances recruitment of the migratory cell to a site of tumor cells in the subject.

According to yet another aspect of the invention, a method for delivering a diagnostic or a therapeutic agent to a pre-selected cell is provided. The pre-selected cells express on their surface a receptor which selectively binds to a biotin conjugate of the invention. According to this aspect of the invention, the method involves contacting a population of cells containing a pre-selected cell (e.g., a leukocyte) with an effective amount of a complex of the invention under conditions to deliver the complex to the pre-selected cell. The complex includes: (a) a biotin conjugate including (i) a biotin covalently coupled to (ii) an agent that selectively binds to a receptor expressed by the pre-selected cell; and (b) an anti-biotin antibody selectively bound to the biotin. The anti-biotin antibody further includes a diagnostic and/or therapeutic agent. Exemplary therapeutic agents include cytotoxic agents such as those described elsewhere in this application. Exemplary diagnostic agents include detectable labels such as those described below. The diagnostic and/or therapeutic agents of the invention are attached to the anti-biotin antibodies in a manner which does not adversely affect the ability of the antibody to selectively bind to biotin.

According to yet another aspect of the invention, a method for modulating (up regulating or down regulating/ desensitizing) a pre-selected chemotactic response is provided. The method involves administering to a subject in need of such treatment a therapeutically effective amount of a biotinylated chemokine agonist or chemokine antagonist to modulate the chemotactic or other chemokine mediated proinflammatory response. The method for modulating a chemokine response can be used to evaluate the role of specific chemokine receptors in various animal models of human disease. The method for modulating a chemokine response also can be used to prevent recruitment and/or activation of resident inflammatory cells, e.g., by administering to a subject in need of such treatment a biotinylated chemokine antagonist of the invention, particularly a biotinylated CXC chemokine antagonist. Additionally, the method can be used to identify specific leukocyte populations which express receptors for chemokines, diagnostic imaging, reagent screening, and creating new animal models of human disease (e.g., by disrupting the normal chemotactic response and observing a change in symptoms in the animal model).

These and other aspects of the invention, as well as various advantages and utilities, will be more apparent with reference to the detailed description of the preferred embodiments and to the accompanying drawings.

All documents referenced in this application are incorporated in their entirety herein by reference.

DETAILED DESCRIPTION OF THE INVENTION

Figure 1:
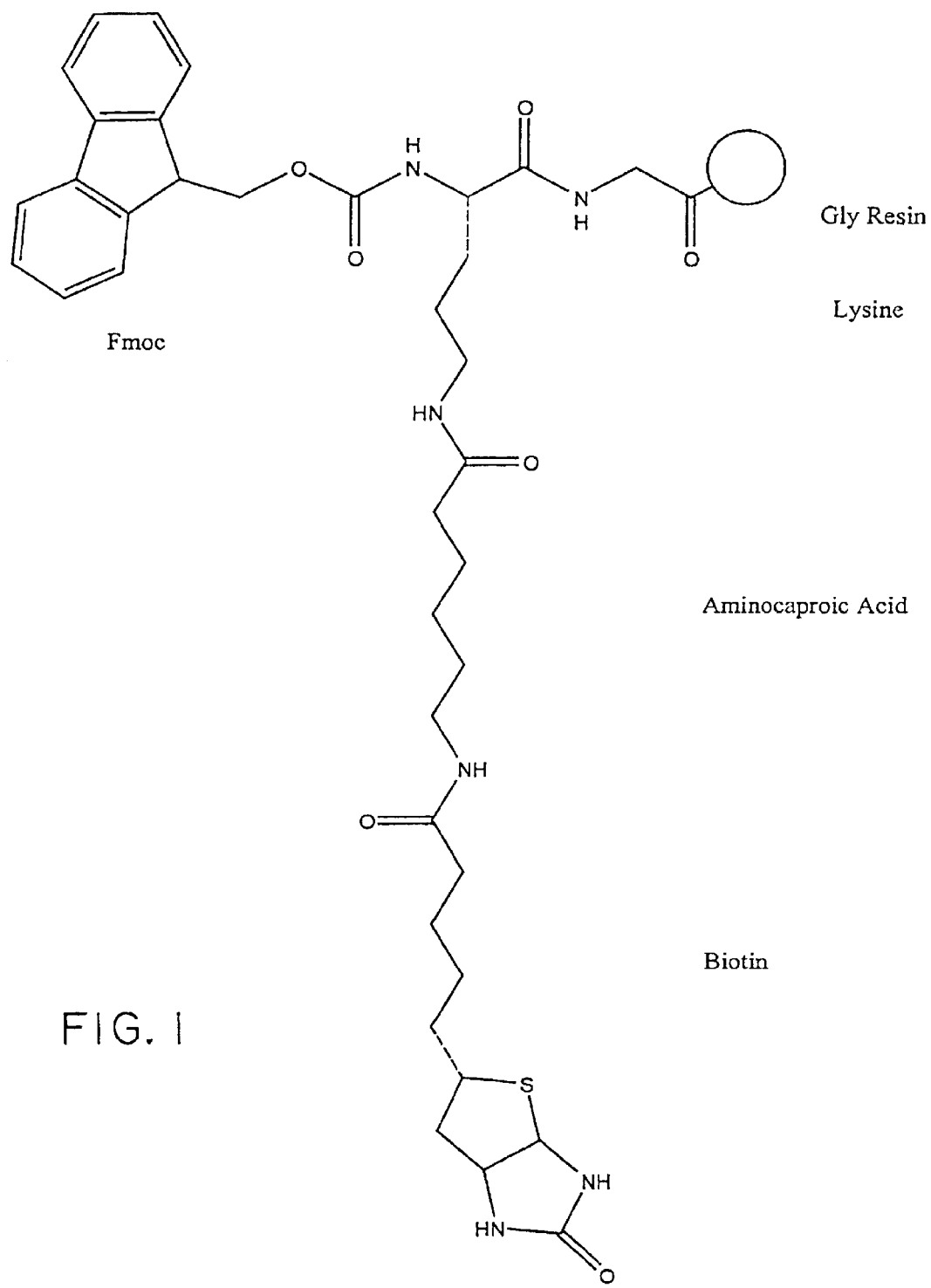
FIG. 1 illustrates an exemplary starting material for synthesis of the biotinylated chemokines of the invention.
Figure 2:
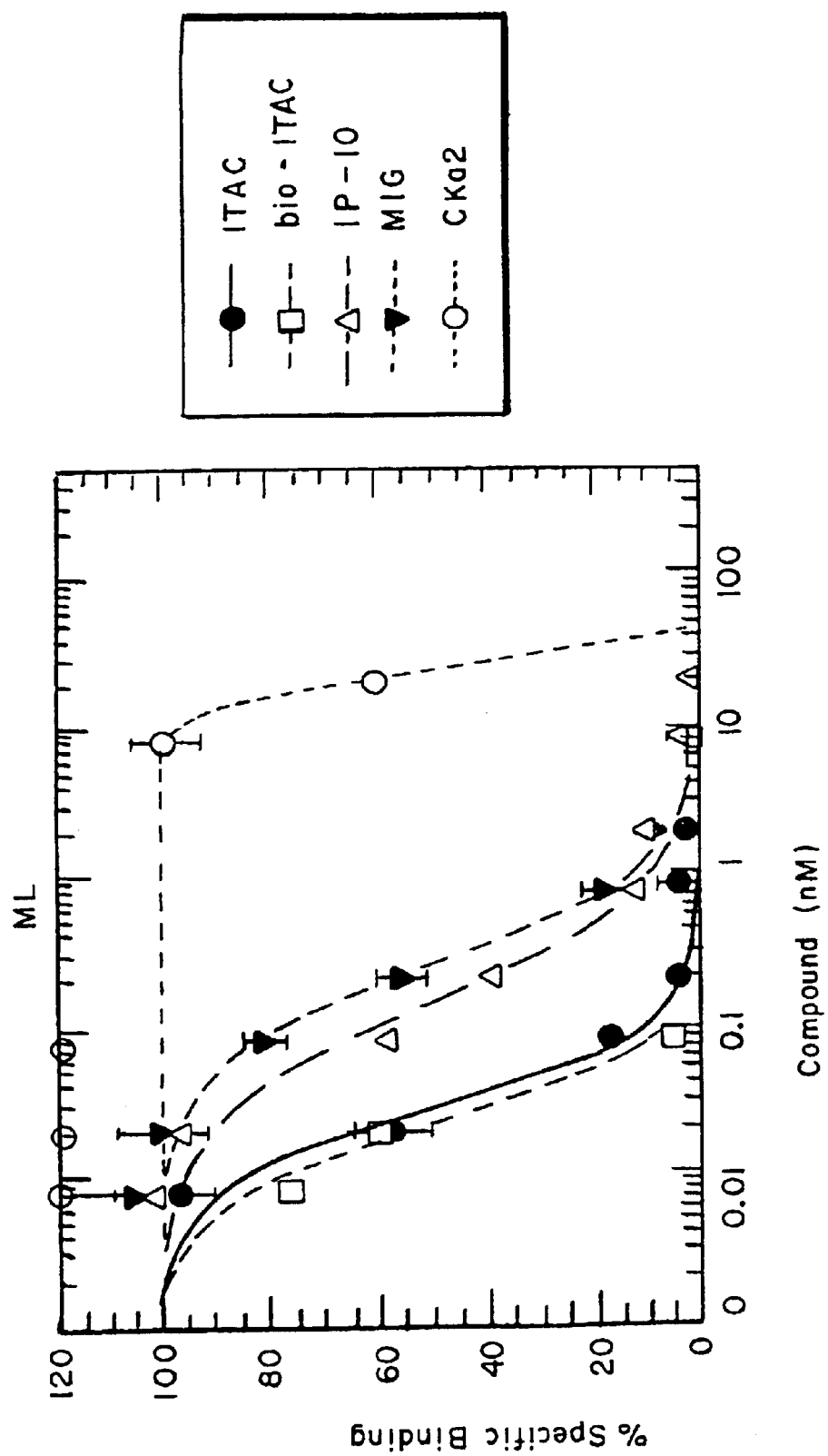
FIG. 2 shows that C-terminally biotinylated ITAC is equivalent to ITAC in binding to CXCR3.
Figure 3:
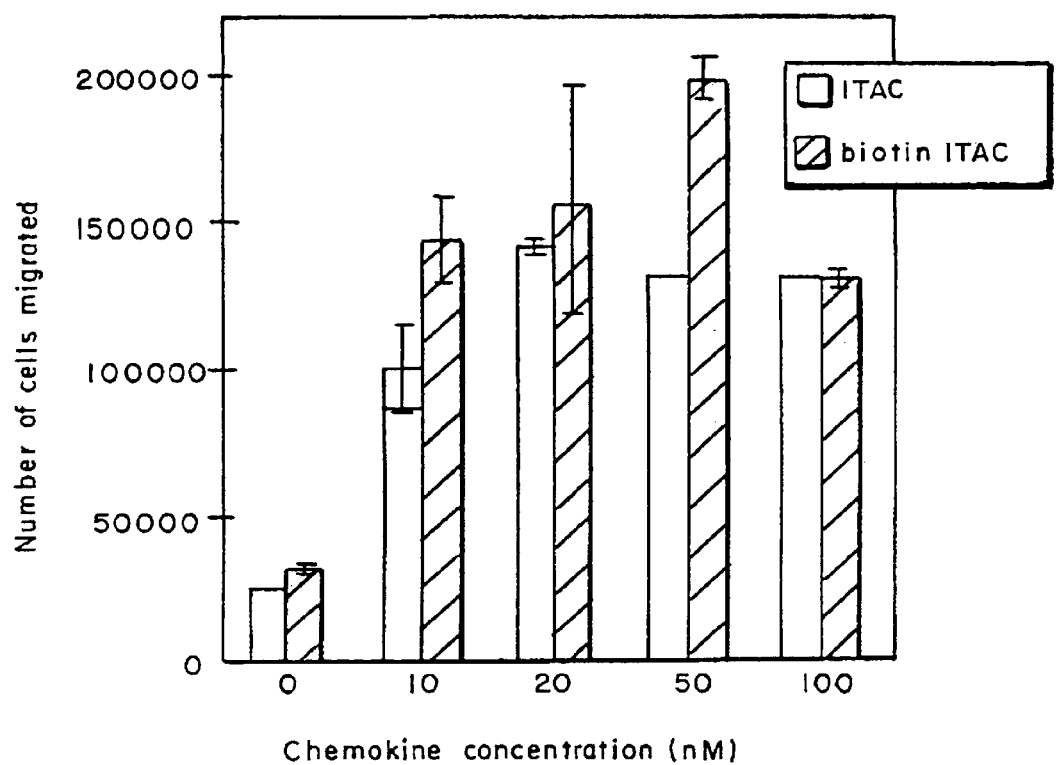
FIG. 3 shows that biotinylated ITAC is equivalent to ITAC in chemotaxis of CXCR3 expressing RBL cells.

The present invention provides a biotinylated-chemokine antibody complex that can be reversibly dissociated in the presence of free biotin. Accordingly, the invention provides a method by which the concentration of a biotinylated-chemokine antibody complex can be adjusted by exposing the complex to varying amounts of free biotin in vivo or in vitro. The complexes of the invention are useful for a variety of applications, including modulating an immune response such as one which is mediated by the chemokine-induced recruitment of migratory cells to a site of inflammation, as well as for the targeted delivery of agents to cells which express a chemokine receptor.

As used herein, a pharmacologically active agent refers to a peptide that binds to a G-protein coupled receptor. The G protein-coupled receptor superfamily (GPCR) is a large group of receptor proteins which share a common structural homology. Exemplary GPCR include the calcium sensing receptor (CSR) and the metabotropic glutamate receptors (mGluRs) (Tanage, Y., et al., Neuron, 1992, 8:169–179; Brown, E., et al., Nature, 1993, 366:575–580); several receptors for glycoprotein hormones (Segaloff, D., et al., Oxf Rev. Reprod Biol., 1992, 14:141–168), pheromones receptors (Ors and VNRs), which are also GPCRs (Buck, L., et al., Cell, 1991, 51:127–133; Dulac, C., et al., Cell, 1995, 83:159–206. Other exemplary peptide ligands that bind to G-protein coupled receptors include Angiotensin; Bradykinin; Bombesin/Neuromedin; C3a; C5a; Calcitonin; Calcitonin Gene Related Peptide; Chemokine; Cholecystokinin; Conopressin; Corticotropin Releasing Factor (CRF); CD55— Decay Accelerating Factor (DAF); Diuretic Hormone Receptors; Endothelin; MLP; FSH Glycoprotein Hormone; Galanin; Growth Hormone Releasing Hormone (GHRH); Growth Hormone Secretagogue (GHS); Gastric Inhibitory Peptide; Gastric Inhibitory Peptide; Glucagon-like Peptide; Glucagon; Gonadotropin Releasing Hormone; LH Glycoprotein Hormone; Melanocortin Receptors; Neuropeptide Y; Neurotensin; Opioid; Oxytocin; Thrombin and Protease Activated; Pituitary Adenylyl Cyclase Activating Peptide; PTH/PTHrP; Secretin; Somatostatin; Tachykinin;

Thyrotropin Releasing Hormone; TSH Glycoprotein Hormone; Vasopressin; Vasotocin; and Vasoactive Intestinal Peptide (VIP).

The pharmacologically active agents are covalently coupled to a biotin in a manner which does not adversely affect the pharmacological activity of the pharmacologically active agent. The binding of a peptide to its cognate G-protein coupled receptor is accompanied by G-protein signal transduction, an event which can be measured using conventional screening assays, such as assays that measure changes in the intracellular concentrations of calcium and/or cyclic nucleotides (see, e.g., PCT Publication No. WO 94/18959, entitled "Calcium Receptor-Active Molecules," to inventors E. Nemeth et al.). The chemokines are a preferred class of pharmacologically active agents. Exemplary and preferred chemokines that are useful in the compositions and methods of the invention include those which are depicted in Table 1.

The Tables are located immediately preceding the claims.

For ease of discussion, the following detailed description of the invention is directed primarily to compositions and methods that include a biotinylated-chemokine as an exemplary biotinylated pharmacologically active agent. It is to be understood that other peptides which bind to G-protein coupled receptors can be substituted for the chemokines described herein to make and use additional biotinylated pharmacologically active agents and complexes of the invention.

According to one aspect of the invention, a composition is provided which includes the following components: (a) a biotin conjugate, including: (i) a biotin covalently coupled to (ii) a pharmacologically active agent; and (b) an anti-biotin antibody. The anti-biotin antibody is selectively bound to the biotin to form a complex of the invention. The composition optionally further includes a pharmaceutically acceptable carrier and may be formulated for a variety of modes of delivery in vivo, including intradermal, intramuscular, intraperitoneal, intravenous, subcutaneous, and controlled-release delivery. The preferred pharmacologically active agents are chemokines.

Biotin is a naturally occurring enzyme cofactor in its L isomeric form. Although it is preferred that L biotin be used for forming the biotin conjugates of the invention, the invention also embraces the D isomeric form of biotin, as well as other biotin derivatives. In general, the biotin is conjugated to the pharmacologically active agent (e.g., chemokine) by way of a linker molecule to form a "biotin conjugate". The linker molecule is selected to have a structure and to provide a sufficient distance between the biotin and the pharmacologically active agent to ensure that the presence of the biotin and/or the linker molecule do not adversely affect the pharmacological activity of the agent. Such linker molecules are well known in the art for coupling peptides and proteins to one another and for the attachment of other functional molecules to proteins. As used herein, a "biotin" refers to the naturally occurring metabolic biotin which is in its L-isomeric form (Sigma Chemical Co., St. Louis, Mo.; Pierce Chemical Co., Rockford, Ill.), as well as the D-isomeric form and modifications of the foregoing biotin molecules. By "modified biotin," it is meant a biotin (either L- or D-isomer) to which a further molecule is coupled in a manner to facilitate the covalent attachment of biotin to the pharmacologically active agent. Typically, modified biotins will refer to a biotin to which a linker molecule is attached.

In general, biotin is coupled to the pharmacologically active peptide via a linker molecule. More specifically, for peptides which are chemokines, biotin is coupled via a linker to the carboxyl terminus of the chemokine. The biotinylated-chemokines of the invention embrace biotin coupled to the complete sequence of the chemokine, as well as biotin coupled to truncated or elongated versions of such peptides (e.g., a chemokine peptide which lacks a portion of its amino terminal or carboxyl terminal sequences). Although not wishing to be bound by any particular mechanism or theory, it is believed that interaction of the chemokine highly basic carboxyl terminus with the negatively charged glucosaminoglycans mediates the cellular uptake of chemokines and that truncation or deletion of the highly basic carboxyl terminus of chemokines can be used create novel chemokine agonists having improved half-life characteristics. The invention also embraces biotinylated truncated or elongated chemokine peptides, in particular, at the amino terminus, for use as chemokine antagonists to inhibit the normal pharmacological activity of the chemokine. (See, e.g., D. Hechtman, et al., J. Immunol. 147(3): 883–892 (1991) which reports an IL-8-like inhibitor of polymorphonuclear leukocyte accumulation at sites of acute inflammation). Such biotinylated truncated chemokine peptides can be used as antagonists to inhibit the normal pharmacological activity of the chemokine. Thus, for example, the biotinylated truncated chemokines of the invention include biotin that is covalently coupled to the carboxyl terminus of a chemokine peptide which lacks a portion of its amino terminal sequence such as the portion N-terminal to the CXC or CC sequence in the CXC and CC families of chemokines, respectively. See, for example, J. Gog, et al., J. Exp. Med. 186:131–137 (1997) which reports a truncated human MCP-1 that functions as an antagonist in a mouse lupus-like disease model.

Linker molecules are used to covalently attach the biotin to the pharmacologically active agent of the invention. Such molecules are discussed in numerous books and catalogues, e.g., Pierce Catalog and Handbook, Rockford, Ill. Typically, these reagents are used to assist in the determination of near-neighbor relationships in proteins, three-dimensional structures of proteins, enzyme-substrate orientation, solid-phase immobilization, hapten-carrier protein conjugation and molecular associations in cell membranes. They also are useful for preparing antibody-enzyme conjugates, immunotoxins and other labeled protein reagents.

For use in accordance with the present invention, it is necessary to maintain the native structure of the pharmacologically active agent. Accordingly, the linker molecules are selected which contain functional groups that couple to amino acid side chains of peptides. Bifunctional reagents (capable of crosslinking biotin to a pharmacologically active agent) are classified on the basis of the following:

1. Functional groups and chemical specificity
2. Length of cross-bridge
3. Whether the cross-linking groups are similar (homobifunctional) or different (heterobifunctional)
4. Whether the groups react chemically or photochemically
5. Whether the reagent is cleavable
6. Whether the reagent can be radio-labeled or tagged with another label.

Reactive groups that can be targeted using a linker molecule include primary amines, sulfhydryls, carbonyls, carbohydrates and carboxylic acids. In addition, any reactive group can be coupled nonselectively using a linker molecule such as photoreactive phenyl azides.

Linker molecules are available with varying lengths of spacer arms or bridges. These bridges connect the two reactive ends. The linker molecules for use in accordance with the instant invention must be selected to minimally inhibit the pharmacological activity of the pharmacologically active agent and the ability biotin to bind to the anti-biotin antibody. Because steric effects dictate the distance between potential reaction sites for cross-liking, different lengths of bridges are required for the interaction. Intermolecular cross-linking is favored with a cross-linker containing a longer space arm about three to about fifteen atoms.

Conformational changes of proteins associated with a particular interaction may also be analyzed by performing cross-linking studies before and after the interaction. A comparison is made by using different arm-length cross-linkers and analyzing the success of conjugation, e g., in screening assays that measure the pharmacological activity of the conjugated agent or that measure the ability of the conjugated agent to bind to its cognate receptor. The use of cross-linkers with different reactive groups and/or spacer arms may be desirable when the conformation of the protein changes such that hindered amino acids become available for cross-linking.

Conjugation reagents contain at least two reactive groups. Homobifunctional cross-linkers can contain at least two identical reactive groups, and heterobifunctional reagents contain two or more different reactive groups. Homobifunctional and heterobifunctional cross-linkers that couple through amines, sulfhydryls or react non-specifically are available from many commercial sources. Exemplary linker molecules that are available from Pierce Co., Rockford, Ill. are shown in Tables 2,3,4, and 5. The tables also identify the group that the linker molecule is reactive toward, e.g., sulfhydryl, amino, etc.

In general, linker molecules are covalently attached to biotin using standard protein coupling techniques which involve coupling a linker molecule to a free amino group, a free sulfhydryl group, or a free carboxyl group. Similarly, the second functional portion of the linker molecule is attached to the chemokine using standard protein coupling chemistry techniques. In general, the linker molecule is attached to the carboxyl terminus of the chemokine. The preferred linker molecules for attachment of a biotin to a chemokine of the invention are those provided in the examples. In general, linker molecules are selected so that attachment of biotin via the linker molecule to the chemokine does not inhibit the ability of the chemokine to bind to its respective receptors as determined in, for example, binding assays such as those disclosed in the examples. Accordingly, the invention also provides a method for selecting linker molecules for use in accordance with the method of the invention, namely, by coupling biotin to a chemokine via a "test" linker molecule and, thereafter, subjecting the biotinylated-chemokine to a pharmacological activity assay or binding assay to determine whether the chemokine has substantially retained its pharmacological activity and/or its ability to bind to its respective receptor.

The biotinylated chemokines of the invention can exhibit an agonist activity or an antagonist activity. By "agonist" is meant a molecule or compound which activates the signaling pathway in question. By "antagonist" is meant a molecule or compound which inhibits the signaling pathway in question. As used herein, a chemokine agonist activity refers to the ability of a chemokine to bind to its cognate receptor and activate the receptor, e.g., by triggering of an intracellular signal. As used herein, a chemokine antagonist activity refers to the ability of a chemokine of the invention to bind to its cognate receptor without activating the receptor and triggering the intracellular signaling events. Accordingly, the chemokine antagonist of the invention can be used to competitively inhibit the binding and activity of a chemokine to its respective receptor in vivo or in vitro and, thereby, inhibit intracellular signaling. Additionally or alternatively, the chemokine agonists of the invention can be used to render cells refractory to further stimulation by circulating chemokines. By "rendering cells refractory," it is meant that the cells are no longer responsive in chemotaxis, $Ca^{2+}$ flux or degranulation assays.

According to one aspect of the invention, a composition ("complex composition") containing a biotin conjugate non-covalently coupled to an anti-biotin antibody to form a complex of the invention is provided. The biotin conjugate includes a biotin covalently coupled to a pharmacologically active agent; and the anti-biotin antibody selectively binds to the biotin to form the complex. The complex compositions of the invention are useful, for example, for modulating an immune response and, in particular, are useful for treating inflammation, enhancing an anti-tumor response, and treating viral infections.

As used herein, an anti-biotin antibody refers to an antibody or antibody fragment that selectively binds to biotin alone, coupled to a linker molecule, or coupled to a pharmacologically active agent of the invention. The anti-biotin antibodies of the invention are selected to bind to biotin and, when complexed, exhibit a half-life of the complex that is significantly shorter than the half-life of an avidin-biotin complex. The half-life of an avidin-biotin complex is on the order of about 200 days in vitro. Thus, in contrast to the avidin-biotin complex, the half-life for the complexes of the invention are at least one-tenth, preferably one-one hundredth, and, more preferably, one-one thousandth of the half-life of the avidin-biotin complex. More particularly, the half-life for a preferred complex of the invention with respect to the dissociation of biotin from the anti-biotin antibody is less than about one hour, more preferably less than about 0.5 hours and, most preferably, less than about 15minutes. Exemplary anti-biotin antibodies that are publicly available and that can be tested in screening assays to determine whether the antibody exhibits an acceptable dissociation rate constant and/or affinity constant for use (or further modification for use) in accordance with present invention are described in H. Bagci, et al., FEBS 322(1): 47–50 (1993). See also, F. Kohen, et al., Meth. in Enzymol. 279:451–463 (1997); Vincent, P., and Samuel, D., J. Immunol. Meth. 165:177–182 (1993); and K. Dakshinamurti, et al., Meth. in Enzymol. 184:111–119 (1990).

Dissociation and association rate constants can be determined using known methods. For example, such rate constants can be measured using the Biacore® systems instrument (Biacore AB, Uppsala, Sweden). According to this method, a ligand, such as a biotinylated chemokine of the invention, is immobilized onto a gold film and a binding protein, such as an anti-biotin antibody, is contacted with the gold film under conditions to allow the binding protein to bind to the ligand. The Biacore® instrument employs a laser to measure the refractive index at the surface of the gold film and to provide real time measurements of the association and dissociation of the binding protein to the immobilized ligand. The instrument is used according to manufacturer's directions to determine the on-rate constant, the off-rate constant, and the affinity constant (the ratio of the on-rate constant to the off-rate constant).

The antibodies of the invention also can be characterized in terms of their affinity constants which can be determined according to conventional methods such as those identified above. In general, the antibodies of the invention have an affinity constant ranging from about 1.0 to about 100.0 nanomolar. Preferably, the anti-biotin antibodies of the invention have an affinity constant ranging from about 1 to about 50 nanomolar and, more preferably, the antibodies have an affinity constant ranging from about 1 to about 10 nanomolar. In contrast, the affinity constant for an avidin-biotin complex (approximately $10^{15}$ M) is several logs higher than those of the antibodies of the invention.

The antibodies of the invention are selected in screening assays which, in part, measure the dissociation rate constant of a biotin-anti-biotin antibody complex. In general, antibody selection is accomplished by performing an ELISA assay that measures the ability of a soluble biotin molecule (e.g., L- or D-biotin, biotin coupled to a linker molecule, or biotin coupled directly or indirectly to a pharmacologically active agent of the invention) to displace or compete with the biotin to which the anti-biotin antibody is bound in the complex. Although the antibodies of the invention are selective for binding to biotin, the specific epitope region to which the anti-biotin antibody binds may include portions of biotin and the linker molecule. Accordingly, the antibodies disclosed herein allow for the competitive binding of soluble biotin to displace or compete with the biotin conjugates that are complexed with the antibodies of the invention in vivo or in vitro. As a result, the complexes of the invention can be dissociated in vivo or in vitro by contacting the complexes with a biotin molecule (e.g., L-biotin) at a concentration that is effective to displace the equilibrium of the complex to allow dissociation of the complex. Antibodies with extremely high affinities for biotin (e.g., greater than about 1 nM to 0.1 nM) are to be avoided for applications which require a reversible reaction, but are preferred for those applications where an extended half-life is desirable as in chronic inflammatory diseases and cancer. An exemplary screening assay for selecting an antibody, which when complexed, has the appropriate half-life constant and the ability to permit complex dissociation is provided in the examples. Thus, the invention provides for the selection of anti-biotin antibodies having particular structural characteristics which allow the antibodies to be used in accordance with the methods of the invention. The invention also permits the selection of linker molecules having the appropriate spacer length to minimize interference with the pharmacological activity of the chemokine to which the biotin is coupled, as well as to select linker molecule primary structures which, when coupled to biotin, can be used to generate monoclonal antibodies that selectively bind to biotin as well as to a portion of the linker molecule. The examples also provide assays for evaluating complex stability in vivo by, for example, measuring the half-life of the complex in vivo, as well as its tissue localization.

Throughout this application, the term "antibody" has been used in its broadest sense to embrace full-length ("intact") antibody molecules, as well as functionally active fragments thereof (e.g., Fab, Fab'$_2$, Fd, scFv, and antibody fragments which include a CDR3 region which binds selectively to a biotin). Antibodies include polyclonal and monoclonal antibodies, prepared according to conventional methodology. Preferably, the antibodies for human therapeutic applications are to human antibodies.

As is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an Fab'$_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarily determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarily determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of nonspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. Thus, for example, PCT International Publication Number WO 92/04381 teaches the production and use of humanized murine RSV antibodies in which at least a portion of the murine FR regions have been replaced by FR regions of human origin. Such antibodies, including fragments of intact antibodies with antigen-binding ability, are often referred to as "chimeric" antibodies.

Thus, as will be apparent to one of ordinary skill in the art, the present invention also provides for Fab'$_2$, Fab, Fv and Fd fragments; chimeric antibodies (e.g., based on the commercially available anti-biotin antibodies) in which the Fc and/or FR and/or CDR1 and/or CDR2 and/or light chain CDR3 regions have been replaced by homologous human or non-human sequences; chimeric F(ab')$_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies, as well as human antibodies derived from libraries such as totally synthetic V gene libraries. In such instances, the biotin or biotin conjugates of the invention, or a fragment thereof, or complexes of biotin can be used to screen peptide libraries, including phage display libraries, to identify and select peptide binding polypeptides that selectively bind to the biotin or biotin conjugates of the invention. Such molecules can be used, as described, for screening assays, for purification protocols, for use in the complexes of the invention to treat inflammation, deliver a diagnostic or therapeutic agent, or modulate a chemotaxis response in vivo or in vitro, and for other purposes that will be apparent to those of ordinary skill in the art.

For treatment where longer half-lives are desirable, the antibodies of the present invention are preferably intact antibody molecules including the Fc region. Such intact antibodies will have longer half-lives than smaller fragment antibodies (e.g., Fab) and are more suitable for intravenous, intraperitoneal, intramuscular, intracavity, subcutaneous, or transdermal administration.

Fab fragments, including chimeric Fab fragments, are preferred in methods in which the peptides of the invention are administered directly to a local tissue environment. For example, the Fab fragments are preferred when the peptide of the invention is administered directly to the site of the tumor or infection. Fabs offer several advantages over $Fab'_2$ and whole immunoglobulin molecules for this therapeutic modality. First, because Fabs have only one binding site for their cognate antigen, the formation of immune complexes is precluded whereas such complexes can be generated when bivalent $Fab'_2$ and whole immunoglobulin molecules encounter their target antigen. This is of some importance because immune complex deposition in tissues can produce adverse inflammatory reactions in certain instances. Second, because Fabs lack an Fc region they cannot trigger adverse inflammatory reactions that are activated by Fc, such as activation of the complement cascade. Third, the tissue penetration of the small Fab molecule is likely to be much better than that of the larger whole antibody. Fourth, Fabs can be produced easily and inexpensively in bacteria, such as *E. coli*, whereas whole immunoglobulin antibody molecules require mammalian cells for their production in useful amounts. Production of Fabs in *E. coli* makes it possible to produce these antibody fragments in large fermenters which are less expensive than cell culture-derived products.

Thus, the invention involves binding polypeptides of numerous size and type that bind selectively to biotin, and conjugates (e.g., with linker molecule and/or with pharmacologically active agent) containing biotin ("biotin conjugate"). These binding polypeptides also may be derived from sources other than antibody technology. For example, such polypeptide binding agents can be provided by degenerate peptide libraries which can be readily prepared in solution, in immobilized form, as bacterial flagella peptide display libraries or as phage display libraries. Combinatorial libraries also can be synthesized of peptides containing one or more amino acids. Libraries further can be synthesized of peptides and non-peptide synthetic moieties.

Alternatively, anti-biotin antibodies of the invention can be selected to enhance clearance, e.g., for applications in which it is desirable to minimize the half-life of a complex in vivo. Depending on the desire to mediate cell clearance versus passive blockade/desensitization of receptors, anti-biotin antibodies of suitable isotypes can be prepared. To achieve this objective, antibody fragments are administered or intact antibodies of a subclass selected from the group consisting of: IgG1, IgG2a, IgG2b, IgG3, IgA, and IgM.

According to yet another embodiment, it may be desirable to select an anti-biotin antibody that is capable of mediating the cross-linking of two receptors on the same or different cell surface. For such applications, it is desirable to employ an anti-biotin antibody which has a greater hinge region flexibility, such as an IgG3 antibody subtype.

For applications which are directed to human therapeutics, it is desirable to have antibodies which are non-antigenic in humans, e.g., human monoclonal antibodies or fragments thereof. For applications which are directed to treating other mammals (e.g., domestic animals (e.g., dogs, cats) and livestock (e.g., cows, sheep, and horses), the biotinylated-chemokine and antibody components of the complex should be selected to be non-antigenic in the species that is being treated.

The antibodies of the invention can be selected for targeted delivery to a pre-selected cell. This selection can be accomplished by selecting an antibody of a particular subgroup (e.g., targeted delivery of the antibody to Fc receptor-bearing cells by virtue of the nature of the Fc domain of the antibody) or by the specificity of an antibody binding domain. For example, the anti-biotin antibodies of the invention optionally include a binding domain which selectively binds to a tumor associated antigen or a viral associated antigen.

As used herein, a "tumor cell associated antigen" is a term of art as used in, for example, International Application No. PCT/US98/01785, (Publication No. WO 98/33914), entitled "Chimeric Antibody Fusion Proteins for the Recruitment and Stimulation of an Anti-Tumor Immune Response," inventors J. Rosenblatt, et al.

Antibodies of the invention which have a dual specificity preferably bind to a tumor cell associated antigen from tumor cells which are breast cancer cells, ovarian cancer cells, lung cancer cells, prostate cancer cells, or other cells which express on their surface a protein which is associated with cancer cell growth. Exemplary tumor cell associated antigens include: carcinoembryonic antigen (tumors of epithelial origin, such as colon, lung, and breast and their metastases), EGF-R (bladder and breast cancer), prostate specific membrane antigen (prostate cancer), GD2 (neuroblastoma), membrane immunoglobulins (lymphomas), and T-cell receptors (T-cell lymphoma). Further, specific examples of tumor cell associated antigens include: proteins such as Ig-idiotype of B cell lymphoma, mutant cyclin-dependent kinase 4 of melanoma, to Pmel-17 (gp100) of melanoma, MART-1 (Melan-A) of melanoma, p15 protein of melanoma, tyrosinase of melanoma, MAGE 1, 2 and 3 of melanoma, thyroid medullary, small cell lung cancer, colon and/or bronchial squamous cell cancer, BAGE of bladder, melanoma, breast, and squamous cell carcinoma, gp75 of melanoma, oncofetal antigen of melanoma; carbohydrate/lipids such as muc1 mucin of breast, pancreas, and ovarian cancer, GM2 and GD2 gangliosides of melanoma; oncogenes such as mutant p53 of carcinoma, mutant ras of colon cancer and HER-2/neu proto-oncogene of breast carcinoma; viral products such as human papilloma virus proteins of squamous cell cancers of cervix and esophagus. See, also, Morioka, et al., J. Immunol. 153:5650 (1994), for additional tumor antigens (e.g., P1A, Connexin 37, MAGE-1, MAGE-3, MART 1/Aa, gp100, Tyrosinase) and/or information relating to the tissue distribution of selected tumor antigens. For example, CD19 on B cells also can be used to target certain leukemias and lymphomas. Additional Melanoma tumor antigen sequences are those reported by Slingluff et al., in Curr. Opin. in Immunol. 6:733–740 (1994); Additional tumor cell antigens that are peptides of the mutated APC gene product are those reported by Townsend et al., in Nature 371:662 (1994)).

In yet other embodiments, the anti-biotin antibodies of the invention have a dual specificity for binding to a viral associated antigen. Exemplary viral associated antigens include: gp120 of HIV, HbsAg, immediate and early genes of hepatitis C virus, CMV, Epstein Barr virus, and respiratory syncytial virus.

The antibodies with dual specificity are useful for the targeted delivery of chemokines to a cell expressing an antigen to which the anti-biotin antibody selectively binds. In this manner, a biotinylated chemokine and, optionally, a further therapeutic or diagnostic agent can be selectively delivered to, for example, cells expressing tumor cell associated antigens or cells/viruses expressing virus associated antigens. In a preferred embodiment of the invention, the antibodies with dual specificity are used to enhance a localized immune response at the site of the tumor cells or virus particles/virus infected cells. For example, the complexes of the invention can be used to enhance a localized TH1 response for treating a cancer by administering a complex of the invention, including a biotinylated-chemokine and an anti-biotin antibody having a binding domain that selectively binds to a tumor cell associated antigen. Targeted delivery of the complex to the tumor cell results in the selective-recruitment of TH1 type cells which express receptors for the chemokine. Exemplary chemokines that bind to receptors expressed on TH 1-type cells include: IP-10, MIG, RANTES, and ITAC.

The anti-biotin antibodies that are useful in the complex for treating cancer have a binding domain that is selective for binding to biotin and at least one other binding domain that is selective for binding to a tumor cell associated antigen. Administration of the complex to a subject having a cancer that is associated with the tumor cell associated antigen is performed to allow targeting of the complex to the tumor cell and, thereby, result in a localized concentration of chemokine at the site of tumor cells. Although not wishing to be bound by any particular theory or mechanism, it is believed that the presence of the elevated chemokine concentration at the site of the tumor cells results in a chemokine gradient which mediates the recruitment of TH1 cells to the site and enhancement of a TH1 immune response to inhibit or prevent further tumor cell growth and/or proliferation. In an analogous manner, other conditions or diseases which flourish as a result of a lack of a TH1 response (e.g., lupus, arthritis) can be treated in this manner. Similarly, diseases or conditions which flourish, in whole or in part, due to a lack of a sufficient TH2 response (e.g., leprosy, asthma, inflammatory bowel diseases such as Crohn's disease and ulcerative colitis, diseases associated with fibrosis such as emphysema and hepatic fibrosis) can be treated in an analogous manner by administering complexes which include a anti-biotin antibody of dual specificity (to target the complex to the diseased cell) and a biotinylated-chemokine which is effective in recruiting and/or binding to receptors located on TH2-type cells. Exemplary chemokines that recruit and/or bind to TH2-type cells include: eotaxin, TARC, and MDC.

The anti-biotin antibodies of the invention optionally include a therapeutic or diagnostic agent attached to the antibody in a manner which does not adversely affect the ability of the antibody to bind to biotin or to a further antigen, if applicable. As used herein, "therapeutic agents" include any therapeutic molecule which desirably is targeted selectively to a cell expressing a tumor cell associated antigen or other infection-associated antigen. Therapeutic agents include antineoplastic agents, radio iodinated compounds, toxins, other cytostatic or cytolytic drugs, and so forth. Antineoplastic therapeutics are well known and include: aminoglutethimide, azathioprine, bleomycin-sulfate, busulfan, carmustine, chlorambucil, cisplatin, cyclophosphamide, cyclosporine, cytarabidine, dacarbazine, dactinomycin, daunorubicin, doxorubicin, taxol, etoposide, fluorouracil, interferon-α, lomustine, mercaptopurine, methotrexate, mitotane, procarbazine HCl, thioguanine, vinblastine sulfate and vincristine sulfate. Additional antineoplastic agents include those disclosed in Chapter 52, Antineoplastic Agents (Paul Calabresi and Bruce A. Chabner), and the introduction thereto, 1202–1263, of Goodman and Gilman's "The Pharmacological Basis of Therapeutics", Eighth Edition, 1990, McGraw-Hill, Inc. (Health Professions Division). Toxins can be proteins such as, for example, pokeweed anti-viral protein, cholera toxin, pertussis toxin, ricin, gelonin, abrin, diphtheria exotoxin, or *Pseudomonas* exotoxin. Toxin moieties can also be high energy-emitting radio nuclides such as cobalt-60. Cytotoxic agents also include, for example, the so-called "suicide" enzymes such as thymidine kinase (TK) and its "suicide" substrate, gangcyclovir, DAB389 EGF (Pickering et. al., *J. Clin. Invest.* 91:724–9 (1993)), and allylamine (Hysmith et al., *Toxicology* 38:141–50 (1986)).

Alternatively, or additionally, the anti-biotin antibodies of the invention further include a diagnostic agent, such as a detectable label. The antibodies may be labeled using radio labels, fluorescent labels, enzyme labels, or free radical labels, using techniques known to the art. The antibodies may be coupled to specific diagnostic labeling agents for imaging of cells and tissues, in vivo or in vitro, that express cancer associated antigens and/or to the above-noted therapeutic agents according to standard coupling procedures. Diagnostic agents include, but are not limited to, barium sulfate, iocetamic acid, iopanoic acid, ipodate calcium, diatrizoate sodium, diatrizoate meglumine, metrizamide, tyropanoate sodium and radio diagnostics including positron emitters such as fluorine-18 and carbon-11, gamma emitters such as iodine-123, technetium-99m, iodine-131 and indium-111, nuclides for nuclear magnetic resonance such as fluorine and gadolinium. The antibodies and complexes of the invention can be used in vivo or in vitro. Accordingly, the detectable labels can include more traditional in vitro labels such as those described herein. Typical fluorescent labels include fluorescein isothiocyanate, rhodamine, phycoerythrin, phycocyanin, allophycocyanin, and fluorescamine. Typical chemiluminescent compounds include luminol, isoluminol, aromatic acridinium esters, imidazoles, and the oxalate esters. Typical bioluminescent compounds include luciferin, and luciferase. Typical enzymes include alkaline phosphatase, β-galactosidase, glucose-6-phosphate dehydrogenase, maleate dehydrogenase, glucose oxidase, and peroxidase. Other diagnostic agents useful in the invention will be apparent to one of ordinary skill in the art.

According to yet another aspect of the invention, a biotin composition is provided which includes a therapeutically effective amount of a biotin and a pharmaceutically acceptable carrier. The biotin composition is useful for reducing the amount of complex in vivo or in vitro. Although not wishing to be bound by any particular theory or mechanism, it is believed that administration of a biotin composition to a subject who has received a complex of the invention results in the displacement of the biotinylated-chemokine from the complex, thereby reducing the effective complex concentration in vivo. Thus, by dissociating the biotinylated-chemokine from the anti-biotin antibody, it is possible to alter the half-life of the biotinylated-chemokine. Accordingly, the biotin compositions are useful for adjusting the concentration of the complex in vivo or in vitro and as a pharmaceutical antidote to terminate therapy, if warranted.

According to yet another aspect of the invention, a composition comprising a therapeutically effective amount of a biotin in a pharmaceutical acceptable carrier is provided. The therapeutically effective amount of biotin is that amount needed to counteract the effect of a complex of the invention. Thus, the biotin compositions disclosed herein are intended for use for adjusting the effective concentration of the complexes of the invention in vivo or in vitro. By administering the biotin compositions to a subject who has received a complex of the invention, the equilibrium equation of the complex, free biotinylated pharmacologically active agent and free antibody can be adjusted. In this manner, administration of free biotin can be used to shift the equilibrium to favor dissociation of the complex.

Preferably, the therapeutically effective amount of biotin in the biotin composition is from about 100 μg to about 100 mg. More preferably, the concentration of biotin in the biotin composition is from about 100 μg to about 10 mg and, most preferably, the concentration of biotin is from about 1 mg to about 10 mg. In general, the concentration of biotin that is administered as a dietary supplement is the U.S. recommended daily allowance of 0.3 mg. In contrast, the concentrations of biotin in the claimed biotin composition are at least 10 fold and, more preferably, 100 fold greater than those which are administered for dietary supplement applications.

According to yet another aspect of the invention, a composition including a mixture of complexes of the invention is provided. The composition contains: (a) a first biotin conjugate comprising (i) a first biotin covalently coupled to (ii) a first agent having a first pharmacological activity; and (b) a second biotin conjugate comprising (i) a second biotin covalently coupled to (ii) a second agent having a second pharmacological activity. The first biotin and the second biotin may be the same or different from one another. For example, the first biotin may be the L isomer and the second biotin may be the D isomer.

The identity of the first and the second agents is dependent upon the particular use to which the mixture of complexes is to be applied. Thus, the mixture of biotin conjugates can further include one or more anti-biotin antibodies to form the complexes of the invention and, optionally, to effect the targeted delivery of the complex to a particular cell population in vivo or in vitro. For example, the anti-biotin antibody can have a dual specificity for biotin and a tumor cell associated antigen. In this example, the first and the second agent can be two different chemokines that mediate the recruitment of different immune system cells to the site of the tumor cell location to enhance a TH1 response to the tumor. Similarly, the mixture of complexes of the invention can be used to effect the targeted delivery of different chemokines to a virus infected cell. In certain preferred embodiments, the composition further includes an anti-biotin antibody which has a dual specificity for binding to biotin and to an antigen expressed on the surface of a pre-selected cell. For example, a first anti-biotin antibody can be used to target a receptor that is expressed on a cytotoxic T-cell (e.g., CD8), and a second anti-biotin antibody can be used to target a receptor that is expressed on a monocyte or a virus-infected cell. In this maimer, complexes of the invention containing the same or different chemokines can be delivered to the same or different cell types.

According to yet another aspect of the invention, a pharmaceutical composition containing a biotin conjugate of the invention and a pharmaceutically acceptable carrier is provided. As used in reference to this particular embodiment, a "pharmaceutically acceptable carrier" is defined below in reference to the pharmaceutical compositions of the invention, preferably, with the further limitation that the pharmaceutically acceptable carriers containing the biotin conjugates exclude buffer preparations which are commonly used in in vitro assays (e.g., phosphate buffered saline). More preferably, the pharmaceutically acceptable carrier for the biotin conjugates of the invention is selected to be used for an intravenous, intraperitoneal, or subcutaneous mode of administration. Accordingly, the therapeutically effective amount of the biotin conjugate also is selected to be suitable for in vivo administration. In general, the therapeutically effective amount of the biotin conjugate is at least 10 fold, more preferably 100 fold, and most preferably 1000 fold greater than the concentration of a biotin conjugate that would be used in connection with an in vitro assay, such as an ELISA assay.

According to yet another aspect of the invention, a therapeutic method which employs the biotinylated chemokines alone or comp!cxed with anti-biotin antibody is provided. The therapeutic method is useful for treating inflammation in a subject in need of such treatment. The method involves administering to a subject a therapeutically effective amount of a complex comprising: (a) a biotin conjugate comprising (i) a biotin covalently coupled to (ii) an agent that selectively binds to a receptor expressed by a pre-selected cell (e.g., a migratory cell); and (b) an anti-biotin antibody selectively bound to the biotin to form a complex. Administration of the complex prevents or reduces inflammation in the subject. Although not wishing to be bound to any particular theory or mechanism, in particular embodiments in which the pre-selected cell is a migratory cell, administration of the complex is believed to result in the inhibition of recruitment of the migratory cell to the site of inflammation. The biotin conjugate and the anti-biotin antibody can be administered simultaneously or sequentially to the subject. The method optionally involves further administering a pharmaceutically acceptable composition of biotin to modulate the effective concentration of the complex in vivo or in vitro (by shifting the equilibrium toward dissociation of the complex). Examples of chemokines, their respective receptors and the migratory cells which express these receptors are provided in Table 1.

According to yet another aspect of the invention, a method to deliver cytotoxic agents to eliminate a specific pre-selected cell (e.g., a leukocyte or virus-infected cell) population is provided. The method can be performed in vivo or in vitro. For example, the method can be used to deliver a cytotoxic agent to a pre-selected cell population prior to infusion of the cell population into a patient. The method also can be used in vitro to desensitize chemokine receptors on pre-selected cells prior to cell reinfusion, e.g., by contacting the cells with a biotin conjugate or complex of the invention at one hour, 37° C. or under other conditions sufficient to desensitize the cell. In this manner, the susceptibility of the treated pre-selected cells to a chemokine gradient in vivo can be inhibited.

The method for delivering a therapeutic agent (e.g., a cytostatic or cytotoxic agent) to a pre-selected cell involves: contacting a population of cells containing a pre-selected cell (e.g., a virus infected cell) with an effective amount of a complex comprising the therapeutic agent under conditions to deliver the therapeutic agent to the pre-selected cell. The complex includes: (a) a biotin conjugate comprising (i) a biotin covalently coupled to (ii) an agent that selectively binds to a receptor expressed by the pre-selected cell; and (b) an anti-biotin antibody selectively bound to the biotin to form the complex. The anti-biotin antibody further comprises the therapeutic agent. The method is performed under conditions whereby contacting the population of cells with the complex allows delivery of the therapeutic agent to the pre-selected cell.

According to a still further aspect of the invention, a method for modulating (up regulating or down regulating/desensitizing) a pre-selected chemotactic response is provided. The method involves administering to a subject in need of such treatment a therapeutically effective amount of a biotinylated chemokine agonist or a biotinylated chemokine antagonist to modulate the chemotactic response. The method is useful for evaluating the role of specific chemokine receptors in various animal models of human disease. Preferably, the complexes include an anti-biotin antibody that has a dual specificity to permit the targeted delivery of the biotinylated chemokine agonist or chemokine antagonist to cells expressing the chemokine receptor.

According to yet another aspect of the invention, a method for identifying specific leukocyte populations which express receptors for chemokines is provided. This method can be used to identify the cognate receptors (and cells expressing the cognate receptors) for chemokines for which receptors have not previously been identified. The method involves contacting the cells suspected of expressing a cognate receptor with a labeled complex of the invention and identifying the receptor and/or cell expressing the receptor to which the complex binds. The receptor can be identified either by immunoprecipitating the cognate receptor or using the responding cells to construct a cDNA library from which to expression clone the receptor from host cells transfectants expressing smaller and smaller pools of cDNAs.

The compositions of the invention are administered in effective amounts. An effective amount is a dosage of the biotinylated pharmacologically active agent or complex of the invention sufficient to provide a medically desirable result. In general, the therapeutically effective amount of a complex of the invention is less than about 10 mg/kg body weight and, more preferably, is from about 1 mg/kg to about 5 mg/kg body weight. However, the effective amount will vary with the particular condition being treated, the age and physical condition of the subject being treated, the severity of the condition, the duration of the treatment, the nature of the concurrent therapy (if any), the specific route of administration and like factors within the knowledge and expertise of the health practitioner. For example, in connection with cancer treatment, an effective amount is that amount which slows or inhibits the growth and/or proliferation of tumor cells that are associated with the cancer. Likewise, an effective amount for treating a viral infection would be an amount sufficient to lessen or inhibit altogether the growth and/or proliferation of infected cells so as to slow or halt the development of or the progression of the infection. Thus, it will be understood that the compositions of the invention can be used to treat the above-noted conditions prophylactically in subjects at risk of developing the foregoing conditions. As used in the claims, "inhibit" embraces all of the foregoing. It is preferred generally that a maximum dose be used, that is, the highest safe dose according to sound medical judgment.

The isolated biotin conjugates and biotin complexes may be administered alone or in combination with alternative (complementary) drug therapies, by any conventional route, including injection or by gradual infusion over time. The administration may, for example, be intravenous, intraperitoneal, intramuscular, intra-cavity, subcutaneous, or transdermal. When using the isolated biotin conjugates and biotin complexes of the invention, direct administration to the tumor or infected cell site is preferred.

The drug therapies are administered in amounts which are effective to achieve the physiological goals (e.g., to prevent or reduce the physiological consequences of cancer, infection, or an aberrant immune response), in combination with the biotin conjugates and biotin complexes of the invention. Thus, it is contemplated that the drug therapies may be administered in amounts which are not capable of preventing or reducing the physiological consequences of the condition being treated when the drug therapies are administered alone but which are capable of preventing or reducing the physiological consequences of the condition being treated when administered in combination with the biotin conjugates and biotin complexes of the invention.

The biotin conjugates and biotin complexes may be administered alone or in combination with the above-described drug therapies as part of a pharmaceutical composition. Such a pharmaceutical composition may include the isolated biotin conjugates and/or biotin complexes in combination with any standard physiologically and/or pharmaceutically acceptable carriers which are known in the art. The compositions should be sterile and contain a therapeutically effective amount of the isolated biotin conjugates and biotin complexes in a unit of weight or volume suitable for administration to a patient. The term "pharmaceutically-acceptable carrier" as used herein means one or more compatible solid or liquid filler, diluents or encapsulating substances which are suitable for administration into a human or other animal. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy. Pharmaceutically acceptable further means a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art.

Compositions suitable for parenteral administration conveniently comprise a sterile aqueous preparation of the biotin conjugates and/or biotin complexes, which is preferably isotonic with the blood of the recipient. This aqueous preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or di-glycerides. In addition, fatty acids such as oleic acid may be used in the preparation of injectables. Carrier formulations suitable for oral, subcutaneous, intravenous, intramuscular, etc. administrations can be found in Remington's Pharmaceutical Sciences, Mack Publishing Co., Easton, Pa. Preservatives and other additives may also be present such as, for example, antimicrobials, anti-oxidants, chelating agents, and inert gases and the like.

A variety of administration routes are available. The particular mode selected will depend, of course, upon the particular drug selected, the severity of the condition being treated, and the dosage required for therapeutic efficacy. The methods of the invention, generally speaking, may be practiced using any mode of administration that is medically acceptable, meaning any mode that produces effective levels of the active compounds without causing clinically unacceptable adverse effects. Such modes of administration include rectal, topical, interdermal, or parenteral routes. The term "parenteral" includes subcutaneous, intravenous, intramuscular, or infusion. Intravenous or intramuscular routes are not particularly suitable for long-term therapy and prophylaxis. They could, however, be preferred in emergency situations. Oral and nasal administration are optional, although less preferred, methods.

The pharmaceutical compositions may conveniently be presented in unit dosage form and may be prepared by any of the methods well-known in the art of pharmacy. All methods include the step of bringing the biotin conjugates and biotin complexes into association with a carrier which constitutes one or more accessory ingredients. In general, the compositions are prepared by uniformly and intimately bringing the biotin conjugates and biotin complexes into association with a liquid carrier, a finely divided solid carrier, or both, and then, if necessary, shaping the product.

Other delivery systems can include time-release, delayed release or sustained release delivery systems. Such systems can avoid repeated administrations of the biotin conjugates and biotin complexes described above, increasing convenience to the subject and the physician. Many types of release delivery systems are available and known to those of ordinary skill in the art. They include the above-described polymeric systems, as well as polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which an agent of the invention is contained in a form within a matrix such as those described in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

Use of a long-term sustained release implant may be particularly suitable for treatment of chronic conditions. Long-term release, are used herein, means that the implant is constructed and arranged to deliver therapeutic levels of the active ingredient for at least 30 days, and preferably 60 days. Long-term sustained release implants are well-known to those of ordinary skill in the art and include some of the release systems described above.

The invention will be more fully understood by reference to the following examples. These examples, however, are merely intended to illustrate the embodiments of the invention and are not to be construed to limit the scope of the invention.

EXAMPLES

Example 1

Preparation of a representative Biotinylated Chemokine

In general, the biotinylated pharmacologically active agents of the invention ("biotin conjugates") are prepared in accordance with routine procedures known to those of ordinary skill in the art or are commercially available. Commercially-available biotinylated chemokines include: biotinylated human MCP-1, human MIP-1 alpha, and human MIP-1 beta (R&D Systems, Minneapolis, Minn.).

Specific protocols are provided below as exemplary methods for preparing a representative biotin conjugate; however, it is to be understood that alternative linker molecules and pharmacologically active agents can be substituted for the particular linker molecules and pharmacologically active agents described in the Examples to make a wide variety of biotin conjugates using no more than routine experimentation. In addition, the biotin conjugates embraced within the scope of the invention can be tested in high throughput screening assays, e.g., ELISA and other calorimetric assays, to select biotin conjugates having the optimum properties (e.g., retention of chemotactic binding activity, optimum binding affinities with anti-biotin antibodies) for use in accordance with the methods of the invention.

(a) Preparation of Biotinylated Chemokines:
Biotinylated chemokines and chemokines in general were synthesized by automated solid phase f-moc chemistry (t-boc chemistry can also be used) using a 433 automated peptide synthesizer (PE Biosystems: Foster City, Calif.). See, e.g., FIG. 1 for an exemplary starting material for synthesis of the biotinylated chemokines of the invention. Special Fsat-moc HBTU cycles were used for the synthesis. The protein was then deprotected and cleaved from the resin by TFA, extracted and purified by preparative reverse-phase HPLC. After purification, the protein was folded and repurified as previously described (Clark-Lewis, I., et al., 1991. Chemical synthesis, purification, and characterization of two inflammatory proteins, neutrophil activating peptide 1 (interleukin-8) and neutrophil activating peptide-2 *Biochemistry*, 30:3128–3135). Biotinylated chemokines were synthesized by incorporating during synthesis an extra C-terminal Lysine derivatized at the $\epsilon$-NH2 group with aminocaproic acid-biotin (f-moc-Lys (aminocaproil-biotin) is commercially available from Calbiochem-Novabiochem, UK). The chemokines described herein were made with the biotin-aminocaproyl-Lys amino acid being the second one starting from the C-terminus. However, this modification can be introduced into any other lysine or lysines in the sequence. By using orthogonally protected Lys residues (e.g., fmoc-Lys(Dde)), any other spacer groups (see tables 2–5) having a carboxyl and an amino functionalities at each end can be used. In general, this synthesis reaction involves a 2-step coupling reaction, in which the spacer group is added to the lysine residue first and then the biotin is coupled to the spacer. In addition, by synthesizing chemokines containing an extra C-terminal cysteine, modifications of this cysteine can be made with any biotin-crosslinker reagents containing sulfhydryl reactive groups (see tables 2–5) for examples of crosslinking reagents). This latter modification can be performed after synthesis, cleavage and folding and purification of the protein.

Example 2

Preparation of an Anti-biotin Antibody

In general, the anti-biotin antibodies of the invention are prepared in accordance with routine procedures known to those of ordinary skill in the art or are commercially available. An exemplary protocol for preparing a monoclonal antibody that selectively binds to biotin with a relatively high affinity ($K_A \sim 10^9 M^{-1}$) is provided in H. Bagci, et al., FEBS 322(1): 47–50 (1993). See also, F.

Kohen, et al., Meth. in Enzymol. 279:451463 (1997); Vincent, P., and Samuel, D., J. Immunol. Meth. 165:177–182 (1993); K. Dakshinamurti, et al., Meth. in Enzymol. 184:111–119 (1990); and Sigma Chemical Co. (St. Louis, Mo., cat. no. #B753, Murine IgG1 α-biotin clone BD-34). In addition, mice transgenic for human Vh and Vl genes are commercially available from Medarex, Annandale, N.J., or from phage display libraries of human Vh and Vl genes, prepared according to the procedure described in M.D. Sheets, et al., PNAS (USA) 95(11): 6157–62 (1998), entitled, "Efficient Construction of a Large Nonimmune Phage Antibody Library: the production of high-affinity human single-chain antibodies to protein antigens".

Protocols are provided below as exemplary methods for preparing a representative anti-biotin antibody; however, it is to be understood that alternative antigenic compositions (containing biotin alone or coupled to linker molecules of various structures and lengths) can be substituted for the particular antigenic compositions described in the Examples to make anti-biotin antibodies having a range of pre-selected kinetic characteristics (e.g., half-life and affinity constants) using no more than routine experimentation.

(a) Identification of Biotin-Specific Monoclonal Antibodies

To produce murine monoclonal antibodies specific for biotin that possess the binding parameters required for in vivo efficacy, we immunize BALB/c mice 3–4× (at two week intervals) with an emulsion of 10–100 μg of immunogen in Freund's Adjuvant. Complete Freund's Adjuvant was used for the first immunization and Incomplete Freund's Adjuvant was used for all subsequent immunizations. The immunogen consists of a soluble chemokine conjugated via an aminocaproic acid linker covalently bound to the ε-amin9 group of a lysine residue added at the carboxyl terminus. Three weeks after the last immunization, the mice are boosted with an intravenous injection of about 10–100 μg of soluble biotinylated chemokine. Four days later the mice are euthanized and the spleen cells fused with an appropriate murine fusion partner in a ratio of about 5–10:1 (spleen:myeloma). The entire fusion is plated in 10 96-well plates and incubated for 8–10 days until the macroscopic appearance of clones. The supernatants are then analyzed according to the following protocol.

(b) Primary Screen

The purpose of the primary screen is to identify all wells containing antibodies that bind conjugated biotin. This is accomplished using an ELISA with biotinylated KLH or BSA coated wells. The biotinylated proteins are coated at concentrations between 2–5 μg/ml in carbonate buffer overnight at 4° C. The wells are blocked for 1–2 hours at 37° C. with a 2% solution of BSA in PBS, then washed in an automated plate washer. Supernatants from each well are incubated for 1 hour at 37° C. then washed in the plate washer. The murine biotin-specific antibodies are detected using a horseradish peroxidase conjugated affinity purified secondary antibody specific for murine IgG; The secondary antibody is incubated for 30 minutes at 37° C., then unbound antibody is washed out in the plate washer. The assay is developed using OPD as a substrate. Cells from wells that are positive in the ELISA are expanded into 24-well plates and the supernatants reassayed in the secondary screen.

(c) Secondary Screen

To identify antibodies with a broad range of binding affinities for conjugated biotin vs. free biotin, each supernatant is assayed in the presence and absence of 0.5 nM biotin to approximate the concentration of biotin in peripheral blood. Supernatants where binding activity is not affected by the presence of soluble biotin are reassayed in the presence of increasing concentrations of a biotinylated chemokine, preferably other than the immunogen, (and/or lysine-aminocaproic acid biotin) vs. free biotin. The assay is developed as in the primary assay. The relative binding ratio is calculated from the concentration of free biotin that results in a 50% reduction in antibody binding/concentration of conjugated biotin that results in a 50% reduction in binding. Clones are grouped according to ratio and representatives from each group are subcloned by limiting dilution. The subclones are re-tested, production is scaled up, and the antibodies purified. The purified antibodies are then assessed for their relative ability to bind conjugated biotin in the presence of free biotin in an ELISA with an immobilized biotinylated chemokine (1 biotin moiety/molecule protein) using the same mass amount of each antibody and increasing concentrations of free biotin. In general, the selection criteria for selecting antibodies for us in accordance with the methods of the invention are as follows. Antibodies useful for therapeutic intervention preferably have an affinity for conjugated biotin 1–4 orders of magnitude greater than the affinity for free biotin. Preferably, the antibody also would be dissociable from the conjugated biotin in the presence of free biotin at higher levels than found in blood. Thus, an increased dietary intake of biotin can be employed as an antidote to dissociate the biotinylated chemokine-MAb complexes when medically necessary. To make full use of this invention, it is desirable to identify antibodies that have varying degrees of affinity for free biotin to tailor the complexes to the individual patients and clinical disease states.

Example 3

Screening Assay for Binding to a Chemokine Receptor

A general protocol for a screening assay is presented below (see FIG. 2 for the results of a representative screening assay).

(a) Ligand Binding Assays.

Competition binding assays were performed with 1251-chemokine as the hot ligand and biotinylated or unbiotinylated chemokine as the cold competitor ligands. The binding reaction was performed with 500,000 receptor cell transfectants and 0.1 nM radiolabeled chemokine in binding buffer (50 mM HEPES<pH 7.5, 1 mM $CaC_{12}$, 5 mM $MgC_{12}$, 0.5% BSA and 0.05% azide) for 1 hour at room temperature in the presence or absence of cold chemokine in a range of 8 different concentrations from 0.0008–20 M. Non-specific binding is determined by residual binding obtained in the presence of 250 nM cold ligand. Cells are then washed with binding buffer containing 0.5 M NaCl and cell associated radioactivity counted with a top count radioactivity counter. Specific binding was calculated by subtracting non-specific binding from the total binding observed at each concentration and IC50 values were calculated by KaleidGraph software.

Example 4

Screening Assay for Chemotaxis Activity in vitro

A general protocol for a screening assay for chemotaxis activity is presented below (see FIG. 3 for the results of a representative screening assay). This assay is predictive of the results obtained in the in vivo chemotaxis assay described below.

(1) Assessment of Chemotactic Activity of Biotinylated Chemokines in vitro

To confirm that the presence of the biotin moiety attached to a c-terminal lysine residue in the chemokine did not interfere with biological activity, a chemotaxis assay was performed in a 24 well transwell plate using L 0.2 transfectants expressing the murine or human form of the cognate chemokine receptor. To perform the assay, increasing concentrations of the unmodified chemokine or the biotinylated form of the chemokine were added to the bottom chamber of appropriate wells in the transwell plate while 1,000,000 chemokine-receptor transfectants were placed in the top chamber. The cells were allowed to migrate for 3–5 hours at 37° C. the filters were then removed, and the cells which migrated into the bottom chamber were resuspended and quantitated by flow cytometric analysis.

(2) Assessment of Chemotactic Activity of Biotinylated Chemokines in vivo

Example 4a

A Model of Leukocyte Recruitment

Figure 4:
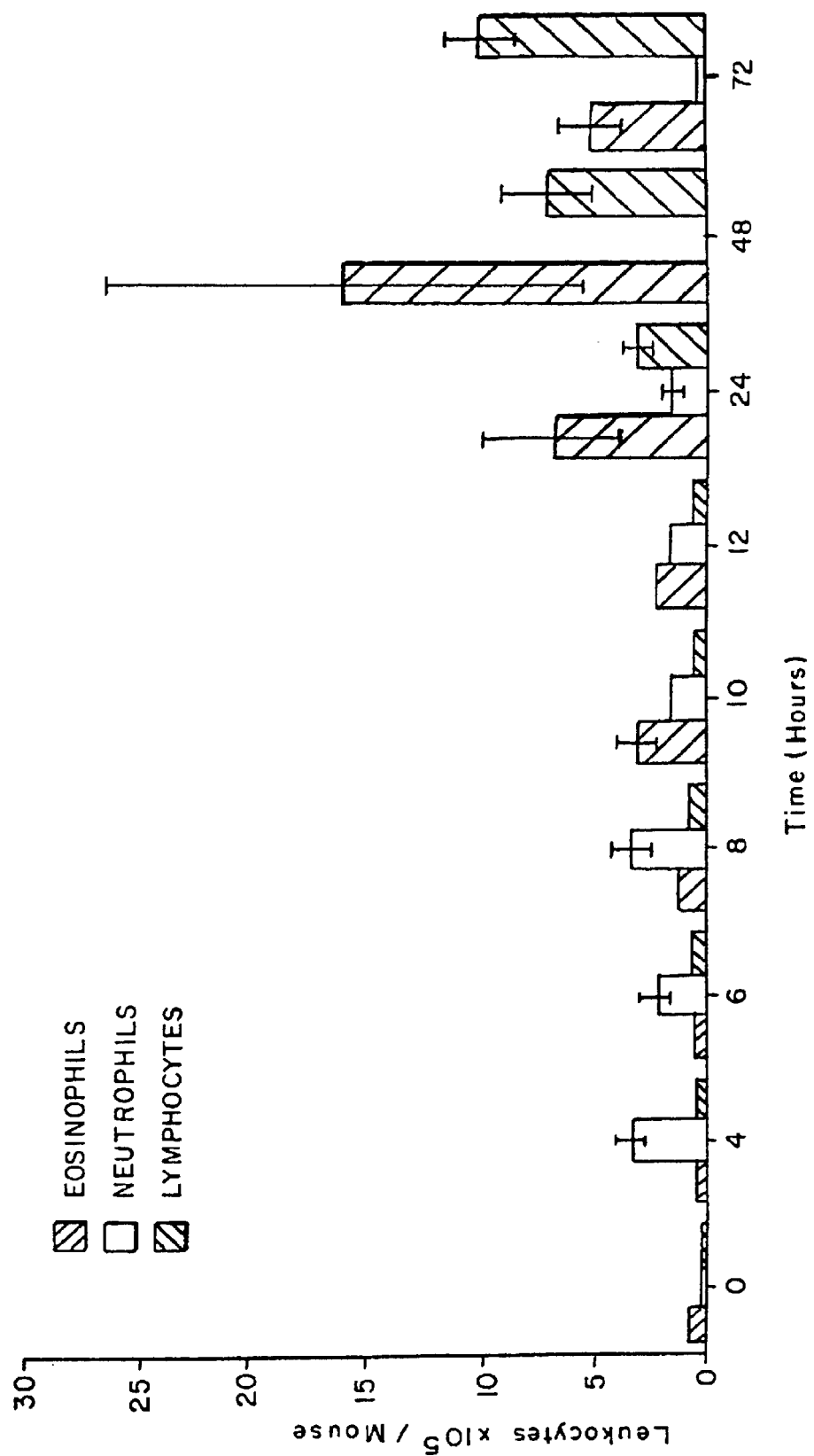
FIG. 4 shows that significant recruitment of eosinophils to the peritoneum does not begin until 8 hours post challenge in an ovalbumin model for eosinophil recruitment into the peritoneum.

To assess the biological activity of the biotinylated chemokine-antibody complexes, the inventors used a model of antigen-induced recruitment of leukocytes to the peritoneum of mice. In this model, mice of the BALB/c or C57B1/6 strain were sensitized by subcutaneous administration on days 0 and 7 with 100 μg of ovalbumin mixed with an adjuvant consisting of 2 mg of aluminum hydroxide. On day 14 the mice were challenged by intraperitoneal administration of 10 ug of soluble ovalbumin. Following the i.p. challenge leukocytes infiltrating into the peritoneum were harvested by peritoneal lavage and the number of each type of leukocyte was determined by differential cell count. As seen in the figure (FIG. 4), three types of leukocytes (eosinophils, neutrophils, lymphocytes) infiltrated into the peritoneum in response to ovalbumin challenge. Neutrophil recruitment occurs early in the response to ovalbumin and peaks between 4–6 hours post challenge. Significant eosinophil recruitment does not begin until approximately 10 hours post challenge and reaches maximum levels 48 hours post challenge. Lymphocyte recruitment is delayed the longest and is maximal by 72 hours post challenge.

Example 4b

Complexes of Biotinylated Eotaxin with Biotin-Specific Antibody

Inhibit Eosinophil Recruitment to the Peritoneum

Figure 5:
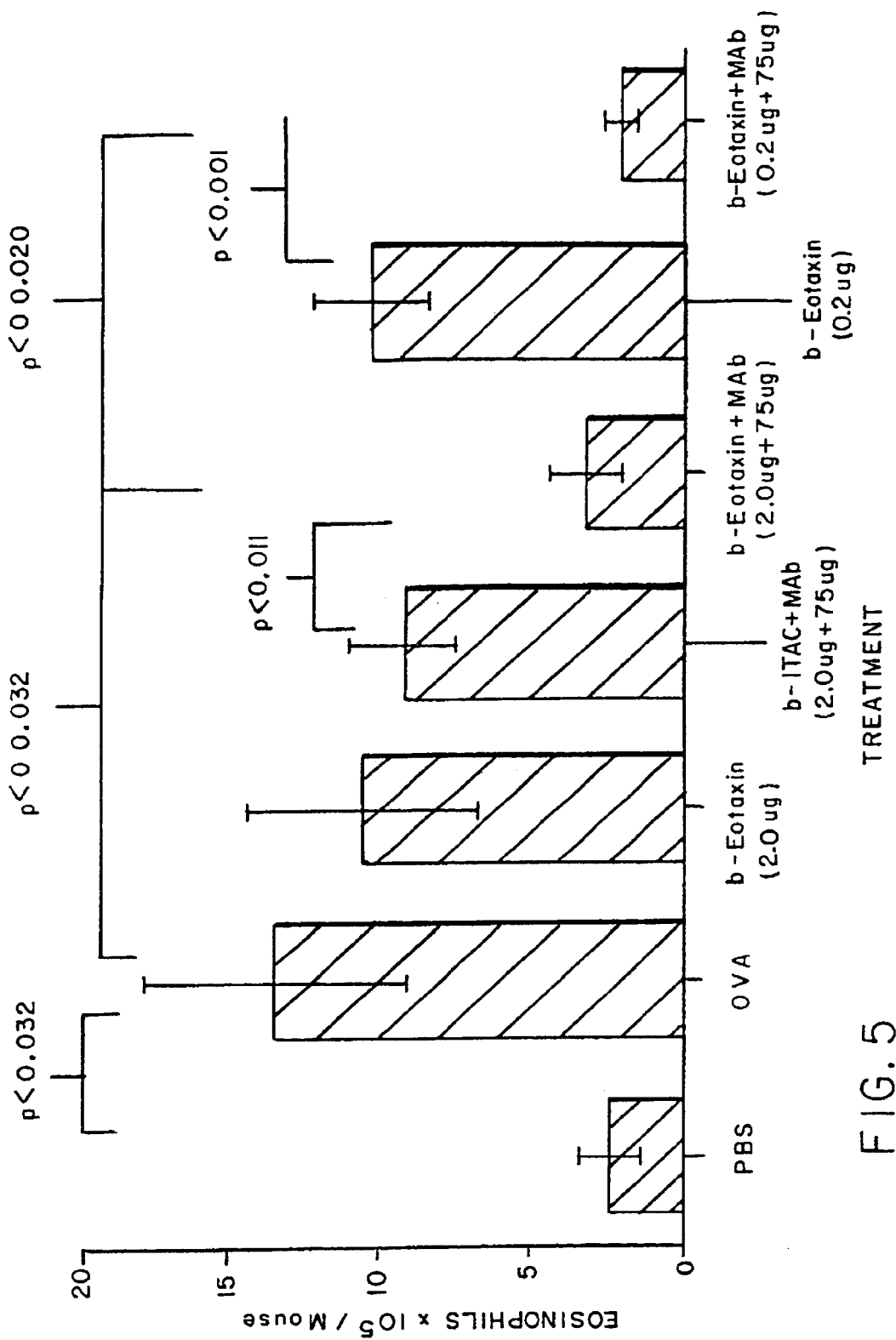
FIG. 5 shows that eosinophil recruitment to the peritoneum of ova-sensitized mice is selectively inhibited by low doses of biotinylated eotaxin complexed with murine anti-biotin antibody at 48 hours post challenge.

Complexes of biotinylated chemokine with the biotin-specific monoclonal antibody are formed ex vivo by mixing 2 ug or 0.2 ug of chemokine with 75 ug of antibody in a volume of 200 μl of saline, PBS or HBSS for 1 hour at 37° C. This represents a molar ratio of antibody to chemokine of 2:1 and 20:1 respectively. The complexes are then administered subcutaneously to ovalbumin sensitized mice 15 minutes prior to i.p. challenge. The effect of biotinylated chemokine/MAb complexes on the recruitment of eosinophils to the peritoneum was assessed at 48 hours post challenge. As seen in the figure (FIG. 5), the biotinylated eotaxin alone had no significant effect on eosinophil recruitment when administered at the high dose (2 μg) or the low dose (0.2 μg). In contrast the complex of biotinylated eotaxin with the biotin-specific monoclonal antibody significantly inhibited eosinophil recruitment. This was true for both the high dose (2 ug) as well as the low dose (0.2 ug) of eotaxin. As a control, complexes of biotinylated ITAC with antibody, produced and administered under identical conditions, had no significant effect on eosinophil recruitment.

Example 4c

Neutrophil Recruitment of the Peritoneum in this Model is

Unaffected by Complexes of Biotinylated Eotaxin or ITAC with Biotin-Specific

Monoclonal Antibodies

Figure 6:
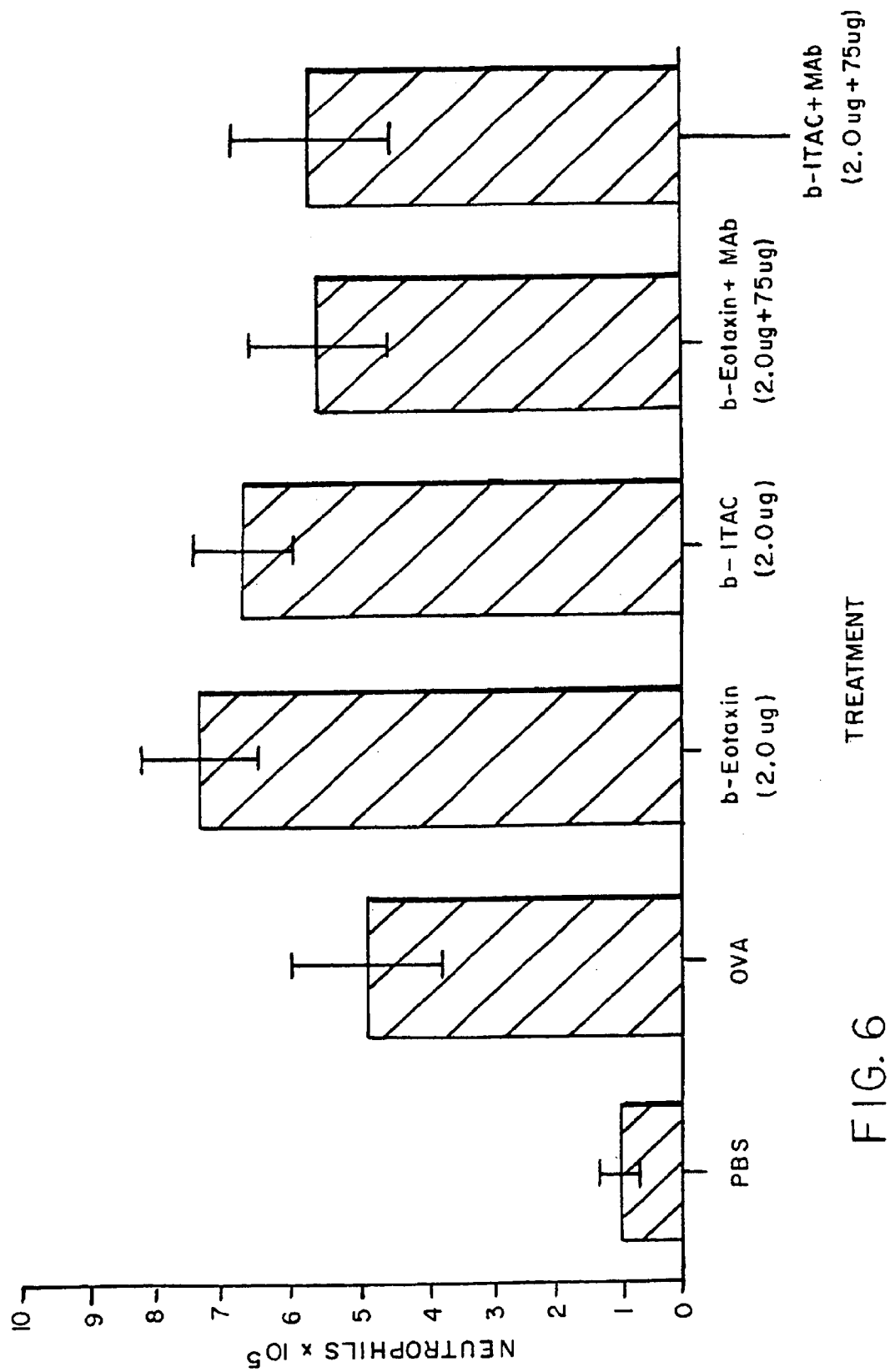
FIG. 6 shows that the complex of biotinylated eotaxin and mouse anti-biotin does not inhibit neutrophil recruitment to the peritoneum in ova-sensitized mice at 6 hours post challenge.

The specificity of this invention was confirmed by evaluating the activity of complexes of eotaxin or ITAC/MAb on neutrophil recruitment to the peritoneum at 6 hours post challenge. Murine neutrophils do not express receptors for eotaxin or ITAC and thus should not be inhibited by either complex. As seen in the figure (FIG. 6), neither complex is capable of inhibiting neutrophil recruitment to the peritoneum in this model.

Example 4d

Lymphocyte Recruitment to the Peritoneum Is Inhibited by

Complexes with Biotinylated ITAC but not Eotaxin

Figure 7:
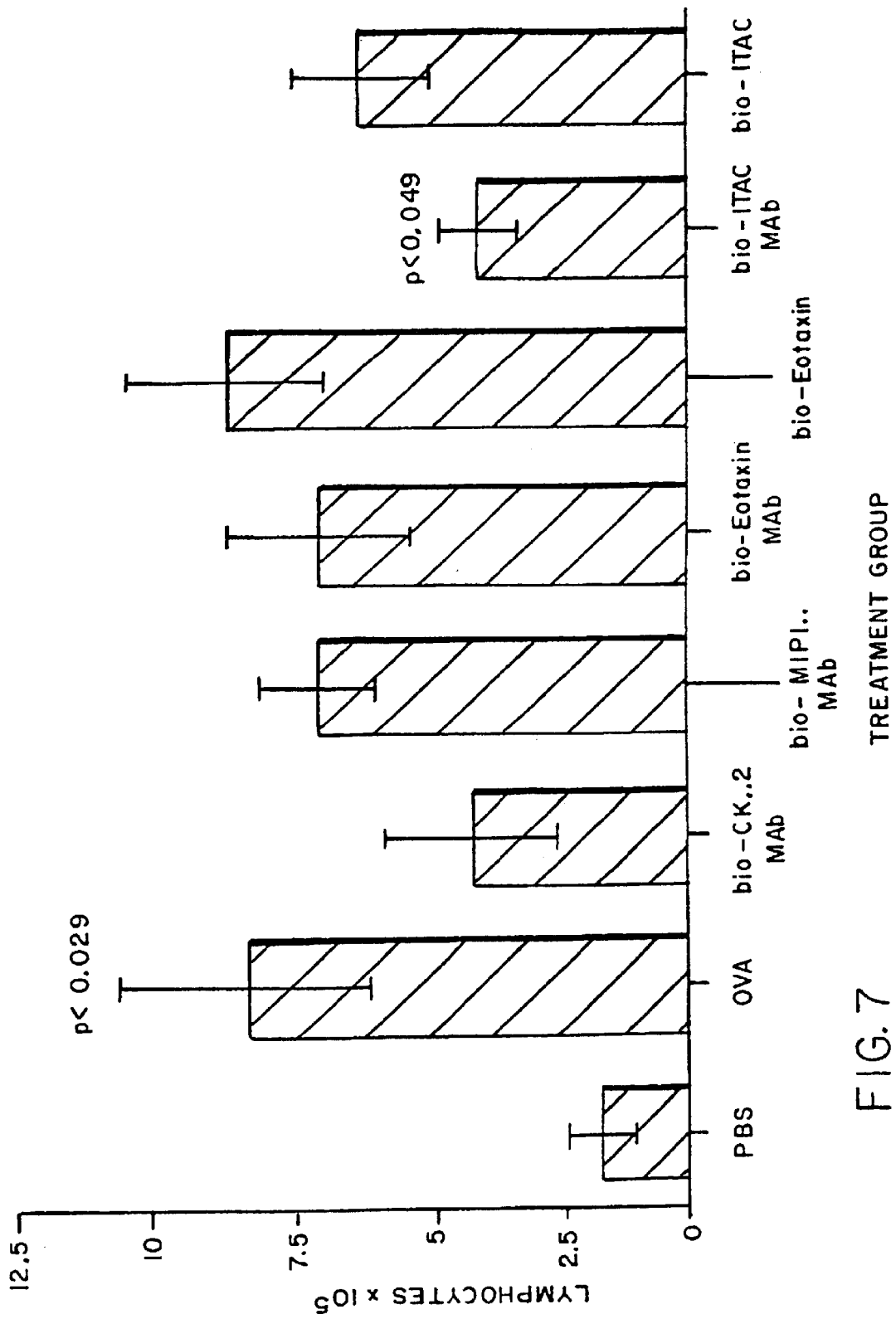
FIG. 7 shows that lymphocyte recruitment to the peritoneum of ova-sensitized and challenged mice is selectively inhibited by biotinylated ITAC but not eotaxin complexed with murine anti-biotin antibody at 72 hours post challenge.

The specificity and broad applicability of this invention is demonstrated in the ability to dissect the role of different chemokine receptors in modulating the recruitment of specific leukocyte populations. As demonstrated in the figure (FIG. 7), complexes of biotinylated eotaxin with Mab had no significant effect on lymphocyte recruitment to the peritoneum at 72 hours. In contrast, complexes of biotinylated ITAC with Mab significantly inhibited lymphocyte recruitment to the peritoneum at 72 hours.

Example 4e

Administration of a Soluble Chemokine In Vivo Can Desensitize

Leukocytes, Bearing the Cognate Receptor, That Are Localized in a Tissue

Figure 8:
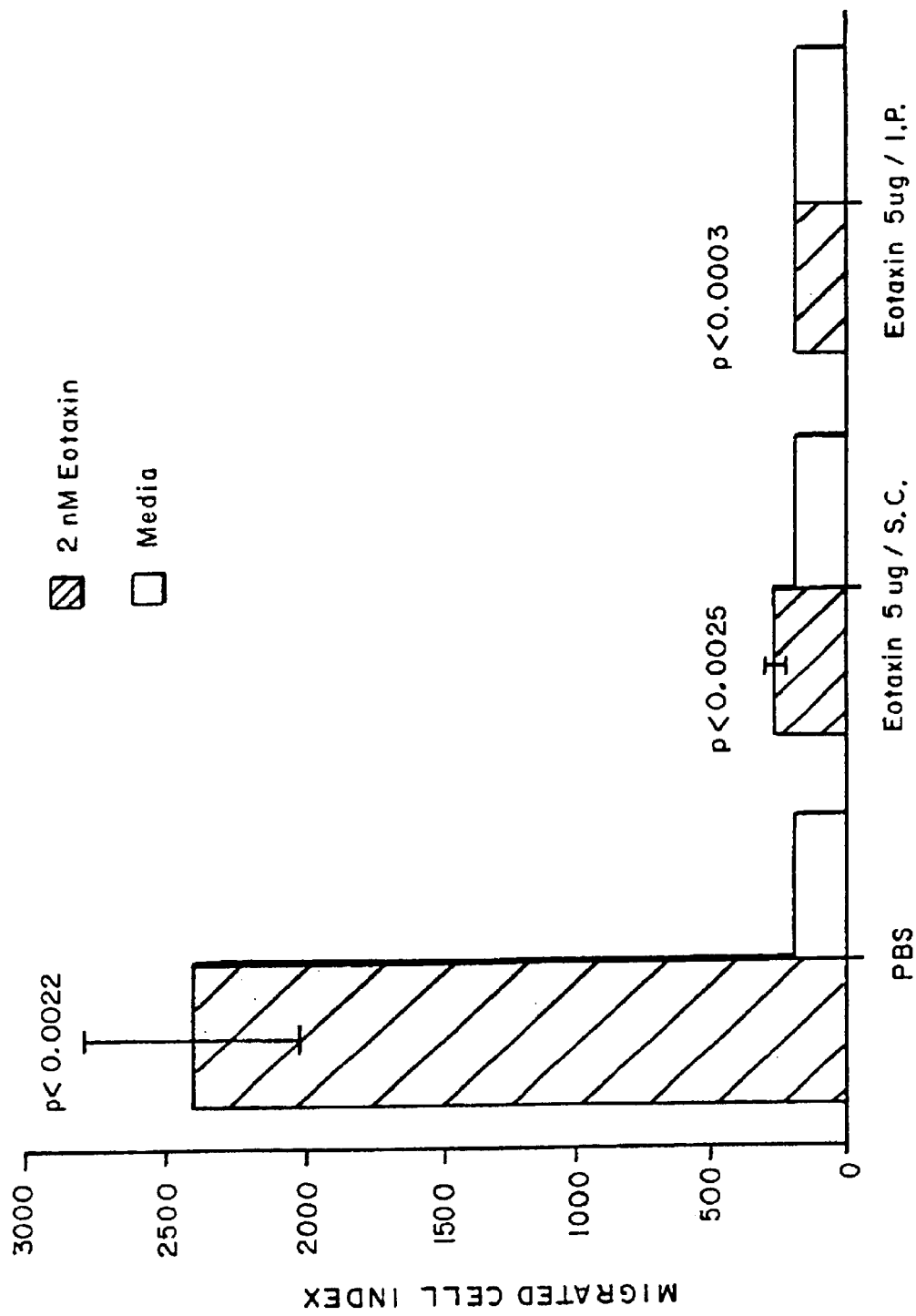
FIG. 8 shows that soluble eotaxin administered 24 hours following ova challenge renders the recruited peritoneal eosinophils refractory to further chemotactic stimuli for at least 24 hours.

Desensitization as a mechanism by which complexes of biotinylated chemokine complexed with biotin-specific monoclonal antibodies inhibit recruitment of leukocytes to tissue was supported by the results of the experiment shown in the figure (FIG. 8). Eosinophils were allowed to infiltrate the peritoneum of ovalbumin sensitized and challenged mice for a period of 24 hours. Soluble eotaxin was then administered 2×, 3 hours apart, either i.p. or s.c. 24 hours post treatment (48 hours post challenge), the eosinophils were harvested from the peritoneum and assessed for their chemotactic potential in vitro. As seen in the figure (FIG. 8), eosinophils from mice treated with PBS had significant and robust chemotaxis to eotaxin compared to media alone. In contrast, eosinophils from mice treated with eotaxin either s.c. or i.p. failed to chemotax or eotaxin suggesting that exposure to eotaxin in vivo had desensitized the eosinophils, rendering them refractory to further stimulation by eotaxin ex vivo.

Conclusions:

In view of the foregoing, we have reached the following conclusions.

S.C. administration of complexes of biotinylated chemokine with anti-biotin Mab can inhibit the recruitment of receptor-bearing leukocytes to tissue following antigenic challenge. The inhibition is specific for leukocyte populations that express the relevant receptor. Preliminary evidence suggests that s.c. administration of a soluble chemokine can result in desensitization in vivo. This experimental approach may have broad applications for investigating the role of a variety of chemokine receptors in inflammatory processes.

Example 5

Evaluation of Complex Stability in Vivo

There are several approaches to measuring the relative amount of complexed chemokine to free chemokine in the blood following administration. One approach is to use an ELISA in which a non-competing chemokine specific monoclonal antibody is immobilized in the well. This is used to capture chemokine from samples of peripheral blood. The amount of antibody still complexed to the chemokine can be assessed using an HRP-conjugated secondary antibody specific of the heavy chain isotype of the biotin-specific monoclonal. Using this technique only biotinylated chemokine complexed to the biotin specific monoclonal antibody will be identified. The stability of the complex can be assessed by following the disappearance of the chemokine-complexed antibody over time. The stability the complex in animal models can be assessed by forming the biotinylated chemokine-MAb complexes with radiolabeled chemokine. Following the collection blood samples at various times post administration, the immunoglobulin fraction of the blood is separated from small molecular weight species such as biotin by precipitation with ammonium sulfate (or by binding to protein G-sepharose beads). The ratio of labeled material in the supernatant relative to the immunoglobulin-containing precipitate (or protein G-sepharose bead associated) is a function of the dissociation rate of the chemokine from the antibody.

It should be understood that the preceding is merely a detailed description of certain preferred embodiments. It therefore should be apparent to those skilled in the art that various modifications and equivalents can be made without departing from the spirit and scope of the invention. It is intended to encompass all such modifications within the scope of the appended claims.

All references, patents and patent publications that are recited in this application are incorporated in their entirety herein by reference.

The Tables are presented below and are followed by what is claimed.

TABLE 1

| CHEMOKINES | | | | |
|---|---|---|---|---|
| Ligand | AKA | Receptor | Active On | Availability |
| | | CC Chemokines | | |
| RANTES | | CCR1, CCR3, CCR5 | mono, T, NK, eos, baso | Pep, R&D, LKS |
| MIP-1a | | CCR1, CCR5 | mono, T, NK | Pep, R&D |

TABLE 1-continued

| CHEMOKINES | | | | |
|---|---|---|---|---|
| Ligand | AKA | Receptor | Active On | Availability |
| MIP-1b | | CCR5 | mono, T, NK | Pep, R&D |
| MCP-1 | | CCR2 | mono, T, NK, baso | Pep, R&D |
| MCP-2 | | CCR2 | mono, T, NK, baso | Pep, R&D |
| MCP-3 | | CCR1, CCR2, CCR3 | mono, T, NK, eos, baso | Pep, R&D |
| MCP-4 | NCC-1, CKb-10 | CCR2, CCR3 | mono, T, eos, baso | Pep, R&D |
| Eotaxin | | CCR3 | eos, baso | Pep, R&D, LKS |
| Eotaxin-2 | MPIF-2, CKb6 | CCR3 | eos, baso | Pep, R&D |
| *TARC | dendrokine | CCR4 | T | Pep, R&D |
| *MDC | STCP-1 | CCR4 | act T, mono, den, NK | Pep |
| MIP-3a | LARC, exodus-1, CKb4 | CCR6 | den, T, lymph | Pep, R&D |
| MIP-3b | ELC, exodus-3, CKb-11 | CCR7 | act B, act T | Pep, R&D |
| I-309 | TCA3 | CCR8 | mono, thy | Pep, R&D |
| HCC-1 | HCC-3, NCC-2, Ckbetal, MIP-1 gamma | CCR1 | mono, CD34 + BM | Pep, R&D |
| HCC-2 | NCC-3, MIP-5, Lkn-1, MIP-1d | ? | neu, mono, lymph | |
| MIP-3 | MPIF-1, CK68 | ? | | |
| MIP-4 | DC-CK1, PARC, AMAC-1 | ? | T | Pep |
| SLC | 6Ckine, exodus-2, TC, A4, PAN EC2 | CCR7 | thy, act T | R&D |
| TECK | | ? | macro, den, thy | |
| LEC | NCC-4, LEC, ILINCK, HCC4 | ? | | |
| CKb-15 | | ? | | |
| PTEC | | ? | | |
| | | CXC Chemokines | | |
| IL-8 | | CXCR1 | neu, NK, T | Pep, LKS, LKS |
| GROa | MGSA-a | CXCR1, CXCR2 | neu, NK | Pep, R&D |
| GROb | MGSA-b, MIP-2a | CXCR1, CXCR2 | neu, NK | Pep, R&D |
| GROg | MIP-2b | CXCR1, CXCR2 | neu, NK | Pep, R&D |
| PF4 | | ? | ? | Pep |

TABLE 1-continued

CHEMOKINES

| Ligand | AKA | Receptor | Active On | Availability |
|---|---|---|---|---|
| NAP-2 | | CXCR2 | neu, NK | Pep |
| ENA78 | | CXCR2 | neu, NK | Pep, R&D |
| GCP2 | | CXCR2 | neu, NK | Pep, R&D |
| **IP-10 | | CXCR3 | act T | Pep, R&D, LKS |
| **MIG | | CXCR3 | act T | Pep, R&D |
| **ITAC | H174, b-R1 | CXCR3 | act T | LKS |
| MIP-2 | | ? | ? | |
| CKa2 | | ? | ? | LKS |
| ADEC | BLC, BCA-1 | CXCR5 | | LKS |
| SDF | | CXCR4 | lymph | Pep, R&D |

CX3C Chemokines

| Ligand | AKA | Receptor | Active On | Availability |
|---|---|---|---|---|
| Fractakine | Neurotactin | CX3CR | T, mono, eos | Pep, R&D, LKS |

C Chemokines

| Ligand | AKA | Receptor | Active On | Availability |
|---|---|---|---|---|
| Lympholactin | | GPR57 | lymph | Pep |

*TH2 chemokines
**TH1 chemokines

KEY FOR TABLE 1
mono = monocytes
eos = eosinophils
baso = basophils
T = T cells
NK = natural killer
Neu = neutrophil
Act = activated
Den = dendritic cell
Thy = thymocytes
act T = activated T cells
act B = activated B cells
lymph = lymphocytes
macro = macrophages

TABLE 2

REACTIVITY OF COMMERCIALLY AVAILABLE CROSS-LINKERS

| Double-Agent Cross-linker | Reactive Towards | | | | | Cleavable By | | | |
|---|---|---|---|---|---|---|---|---|---|
| | —NH₂ | —SH | | Non-selective (Photo- | —COOH | | | | |
| Acronym | Aminos | Sulfhydryls | Carbohydrates | reactive) | Carboxyls | Thiols | Base | Periodate | Hydroxylomine |
| ABH | | | X | X | | | | | |
| ANB-NOS | X | | | X | | | | | |
| APDP | | X | | X | | X | | | |
| APG | | | | X | | | | | |
| ASIB | | X | | X | | | | | |
| ASBA | | | | X | X | | | | |
| BASED | | | | X | | X | | | |
| BS³ | X | | | | | | | | |
| BMH | | X | | | | | | | |
| BSOCOES | X | | | | | | | X | |
| DFDNB | X | | | | | | | | |
| DMA | X | | | | | | | | |
| DMP | X | | | | | | | | |
| DMS | X | | | | | | | | |
| DPDPB | | X | | | | X | | | |
| DSG | X | | | | | | | | |
| DSP | X | | | | | X | | | |

TABLE 3

REACTIVITY OF COMMERCIALLY AVAILABLE CROSS-LINKERS

| | Reactive Towards | | | | | Cleavable By | | | |
|---|---|---|---|---|---|---|---|---|---|
| Double-Agent Cross-linker Acronym | —NH₂ Aminos | —SH Sulfhydryls | Carbohydrates | Non-selective (Photo-reactive) | —COOH Carboxyls | Thiols | Base | Periodate | Hydroxylomine |
| DSS | X | | | | | | | | |
| DST | X | | | | | | | X | |
| DTBP | X | | | | | X | | | |
| DTSSP | X | | | | | X | | | |
| EDC | X | | | | X | | | | |
| FGS | X | | | | | | | | X |
| GMBS | X | X | | | | | | | |
| HSAB | X | | | X | | | | | |
| LC-SPDP | X | X | | | | | | | |
| MBS | X | X | | | | X | | | |
| M₂C₂H | | X | X | | | | | | |
| MPBH | | X | X | | | | | | |
| NHS-ASA | X | | | X | | | | | |
| PDPH | | X | X | | | X | | | |
| PNP-DTP | X | | | X | | | | | |
| SADP | X | | | X | | X | | | |
| SAED | X | | | X | | X | | | |
| SAND | X | | | X | | X | | | |

TABLE 4

REACTIVITY OF COMMERCIALLY AVAILABLE CROSS-LINKERS

| | Reactive Towards | | | | | Cleavable By | | | |
|---|---|---|---|---|---|---|---|---|---|
| Double-Agent Cross-linker Acronym | —NH₂ Aminos | —SH Sulfhydryls | Carbohydrates | Non-selective (Photo-reactive) | —COOH Carboxyls | Thiols | Base | Periodate | Hydroxylomine |
| SANPAH | X | | | X | | | | | |
| SASD | X | | | X | | X | | | |
| SDBP | X | | | | | | | | |
| SIAB | X | X | | | | | | | |
| SMCC | X | X | | | | | | | |
| SMBP | X | X | | | | | | | |
| SMPT | X | X | | | | | | | |
| SPDP | X | X | | | | X | | | |
| Sulfo-BSOCOES | X | | | | | | X | | |
| Sulfo-DST | X | | | | | | | X | |
| Sulfo-EGS | X | | | | | | | | X |
| Sulfo-GMBS | X | X | | | | | | | |
| Sulfo-HSAB | X | | | X | | | | | |
| Sulfo-LC-SPDP | X | X | | | | X | | | |
| Sulfo-MBS | X | X | | | | | | | |
| Sulfo-NHS-ASA | X | | | X | | | | | |
| Sulfo-NHS-LC-ASA | X | | | X | | | | | |
| Sulfo-SADP | X | | | X | | X | | | |

TABLE 5

REACTIVITY OF COMMERCIALLY AVAILABLE CROSS-LINKERS

| | Reactive Towards | | | | | Cleavable By | | | |
|---|---|---|---|---|---|---|---|---|---|
| Double-Agent Cross-linker Acronym | —NH₂ Aminos | —SH Sulfhydryls | Carbohydrates | Non-selective (Photo-reactive) | —COOH Carboxyls | Thiols | Base | Periodate | Hydroxylomine |
| Sulfo-SAMC | X | | | X | | | | | |
| Sulfo-SANPAH | X | | | X | | | | | |
| Sulfo-SAPB | X | | | X | | | | | |
| Sulfo-SIAB | X | X | | | | | | | |
| Sulfo-SMCC | X | X | | | | | | | |

TABLE 5-continued

REACTIVITY OF COMMERCIALLY AVAILABLE CROSS-LINKERS

| Double-Agent Cross-linker | Reactive Towards | | | | | Cleavable By | | | |
|---|---|---|---|---|---|---|---|---|---|
| | —NH$_2$ | —SH | | Non-selective (Photo- | —COOH | | | | |
| Acronym | Aminos | Sulfhydryls | Carbohydrates | reactive) | Carboxyls | Thiols | Base | Periodate | Hydroxylomine |
| Sulfo-SMBP | X | X | | | | | | | |
| Sulfo-LC-SMPT | X | X | | | | | | | |

What is claimed is:

1. A composition comprising:
   (a) a biotin conjugate comprising:
      (i) a biotin covalently coupled to
      (ii) a pharmacologically active chemokine; and
   (b) an anti-biotin antibody selectively bound to said biotin to form a complex.

2. The composition of claim 1, wherein the pharmacologically active chemokine has an agonist activity.

3. The composition of claim 1, wherein the pharmacologically active chemokine has an antagonist activity.

4. The composition of claim 1, wherein the complex has a half-life ranging from about 15 minutes to about 1 hour in the presence of supra physiological levels of biotin and the anti-biotin antibody has an affinity constant ranging from about 1.0 to about 100.0 nanomolar.

5. The composition of claim 1, wherein the anti-biotin antibody comprises a therapeutic agent that is a cytotoxic agent.

6. The composition of claim 1, wherein the anti-biotin antibody comprises a diagnostic agent attached thereto.

7. The composition of claim 1, wherein the anti-biotin antibody has a dual specificity.

8. The composition of claim 7, wherein the anti-biotin antibody selectively binds to a tumor cell associated antigen.

9. The composition of claim 7 wherein the anti-biotin antibody selectively binds to a viral associated antigen.

10. A composition comprising:
    (a) a biotin conjugate comprising
       (i) a biotin covalently coupled to
       (ii) a chemokine having a pharmacological activity; and
    (b) a pharmaceutically acceptable carrier, wherein the pharmaceutically acceptable carrier is suitable for parenteral administration.

11. The composition of claim 1, wherein the composition is lyophilized.

12. The composition of claim 1, further comprising a pharmaceutically acceptable carrier.

13. The composition of claim 12, wherein the pharmaceutically acceptable carrier is acceptable for a mode of delivery selected from the group consisting of: intradermal delivery, intramuscular delivery, intraperitoneal delivery, intravenous delivery, subcutaneous delivery, and controlled release delivery.

14. The composition of claim 1, wherein the biotin is selected from the group consisting of L-biotin, D-biotin and derivative thereof.

15. The composition of claim 1, wherein the chemokine is selected from the group consisting of the chemokines RANTES, MIP-1alpha, MIP-1 beta, MCP-1, MCP-2, MCP-3, MCP-4, eotaxin, eotaxin-2, TARC, MDC, MIP-3alpha, MIP-3beta, I-309, HCC-1, HCC-2, MIP-3, MIP-4, SLC, TECK, LEC, CKb-15, PTEC, IL-8, GROalpha, GRObeta, GROgamma, PF4, NAP-2, ENA-78, GCP2, IP-10, MIG, ITAC, MIP-2, CKa2, ADEC, SDF, fractakine and lvmpholactin.

16. The composition of claim 1, wherein the chemokine has a carboxyl terminus and the biotin is covalently attached to the carboxyl terminus of the chemokine.

17. The composition of claim 1, wherein the biotin is covalently coupled to the pharmacologically active chemokine via a linker molecule.

18. The composition of claim 1, wherein the complex has a half-life ranging from about 15 minutes to about 1 hour in the presence of supra physiological levels of biotin.

19. The composition of claim 1, wherein the anti-biotin antibody has an affinity constant ranging from about 1.0 to about 100.0 nanomolar.

20. The composition of claim 1, wherein the anti-biotin antibody is selected from the group consisting of an intact antibody, and an antibody fragment.

21. The composition of claim 1, wherein the anti-biotin antibody is a human antibody or fragment thereof.

22. The composition of claim 1, wherein the anti-biotin antibody has a subclass selected from the group consisting of a IgG1 subclass, and an IgG3 subclass.

23. The composition of claim 1, wherein the anti-biotin antibody comprises a therapeutic agent attached thereto.

24. The composition of claim 1, wherein the complex has a half-life of from one day to one month in vivo.

25. The composition of claim 1, wherein the complex has a half-life of from one week to two weeks in vivo.

26. The composition of claim 10, wherein the chemokine having a pharmacological activity has an agonist activity.

27. The composition of claim 10, wherein the chemokine having a pharmacological activity has an antagonist activity.

28. The composition of claim 10, wherein the composition is lyophilized.

29. The composition of claim 10, wherein the biotin is selected from the group consisting of L-biotin, D-biotin and derivative thereof.

30. The composition of claim 10, wherein the chemokine is selected from the group consisting of the chemokines RANTES, MIP-1 alpha, MIP-1 beta, MCP-1, MCP-2, MCP-3, MCP-4, eotaxin, eotaxin-2, TARC, MDC, MIP-3alpha, MIP-3beta, 1–309, HCC-1, HCC-2, MIP-3, MIP4, SLC, TECK, LEC, CKb-15, PTEC, IL-8, GROalpha, GRObeta, GROgamma, PF4, NAP-2, ENA-78, GCP2, IP-10, MIG, ITAC, MIP-2, CKa2, ADEC, SDF, fractakine and lympholactin.

31. The composition of claim 10, wherein the chemokine has a carboxyl terminus and the biotin is covalently attached to the carboxyl terminus of the chemokine.

32. The composition of claim 10, wherein the biotin is covalently coupled to the chemokine having a pharmacological activity via a linker molecule.

33. The composition of claim 1, wherein the chemokine is ITAC.

34. The composition of claim 1, wherein the chemokine is eotaxin.

35. The composition of claim 1, wherein the chemokine is MDC.

36. The composition of claim 1, wherein the chemokine is MIP-3alpha.

37. The composition of claim 1, wherein the chemokine is MIP-2.

38. The composition of claim 1, wherein the chemokine is MIP-1beta.

39. The composition of claim 1, wherein the chemokine is MCP-1.

40. The composition of claim 1, wherein the chemokine is MIP-1alpha.

41. The composition of claim 1, wherein the chemokine is RANTES.

42. The composition of claim 1, wherein the chemokine is I-309.

43. The composition of claim 10, wherein the chemokine is ITAC.

44. The composition of claim 10, wherein the chemokine is eotaxin.

45. The composition of claim 10, wherein the chemokine is MDC.

46. The composition of claim 10, wherein the chemokine is MIP-3alpha.

47. The composition of claim 10, wherein the chemokine is MIP-2.

48. The composition of claim 10, wherein the chemokine is MIP-1beta.

49. The composition of claim 10, wherein the chemokine is MCP-1.

50. The composition of claim 10, wherein the chemokine is MIP-1alpha.

51. The composition of claim 10, wherein the chemokine is RANTES.

52. The composition of claim 10, wherein the chemokine is I-309.

53. The composition of claim 1, wherein the chemokine is a full-length chemokine.

54. The composition of claim 1, wherein the chemokine is a truncated chemokine.

55. The composition of claim 1, wherein the chemokine is an elongated chemokine.

56. The composition of claim 54, wherein the truncated chemokine is truncated at an amino terminus.

57. The composition of claim 54, wherein the truncated chemokine is truncated at a carboxy terminus.

58. The composition of claim 55, wherein the elongated chemokine is elongated at an amino terminus.

59. The composition of claim 10, wherein the chemokine is a full-length chemokine.

60. The composition of claim 10, wherein the chemokine is a truncated chemokine.

61. The composition of claim 10, wherein the chemokine is an elongated chemokine.

62. The composition of claim 60, wherein the truncated chemokine is truncated at an amino terminus.

63. The composition of claim 60, wherein the truncated chemokine is truncated at a carboxy terminus.

64. The composition of claim 61, wherein the elongated chemokine is elongated at an amino terminus.

65. The composition of claim 2 wherein the pharmacologically active chemokine is chemokine truncated at the carboxy terminus.

66. The composition of claim 3, wherein the pharmacologically active chemokine is a chemokine truncated or elongated at the amino terminus.

67. The composition of claim 26, wherein the chemokine having a pharmacological activity is a chemokine truncated at the carboxy terminus.

68. The composition of claim 27, wherein the chemokine having a pharmacological activity is a chemokine truncated or elongated at the amino terminus.

* * * * *

UNITED STATES PATENT AND TRADEMARK OFFICE
CERTIFICATE OF CORRECTION

PATENT NO. : 6,869,606 B1
DATED : March 22, 2005
INVENTOR(S) : Newman et al.

It is certified that error appears in the above-identified patent and that said Letters Patent is hereby corrected as shown below:

Column 36,
Lines 16 and 17, delete "Ivmpholactin" and insert therefor -- lympholactin --.
Line 55, delete "1-309," and insert therefor -- I-309, --.

Column 38,
Line 26, delete "chemokine is chemokine" and insert therefor -- chemokine is a chemokine --.

Signed and Sealed this

Thirty-first Day of May, 2005

JON W. DUDAS
*Director of the United States Patent and Trademark Office*